US010398143B2

(12) United States Patent
Graber et al.

(10) Patent No.: US 10,398,143 B2
(45) Date of Patent: Sep. 3, 2019

(54) MELANOIDINS AND THEIR USE FOR IMPROVING PROPERTIES OF PLANTS

(71) Applicant: The State of Israel, Ministry of Agriculture & Rural Development, Agricultural Research Organization (ARO) (Volcani Center), Bet-Dagan (IL)

(72) Inventors: Ellen R. Graber, Rehovot (IL); Yigal Elad, Givat Shmuel (IL); Dalia Rav David, Nes Tziona (IL); Sergey Segal, Ramat Gan (IL)

(73) Assignee: THE STATE OF ISRAEL, MINISTRY OF AGRICULTURE DEVELOPMENT, AGRICULTURAL RESEARCH ORGANIZATION (ARO) (VOLCANI CENTER), Bet-Dagan (IL)

( * ) Notice: Subject to any disclaimer, the term of this patent is extended or adjusted under 35 U.S.C. 154(b) by 0 days.

(21) Appl. No.: 14/760,704

(22) PCT Filed: Jan. 14, 2014

(86) PCT No.: PCT/IL2014/050047
§ 371 (c)(1),
(2) Date: Jul. 13, 2015

(87) PCT Pub. No.: WO2014/111932
PCT Pub. Date: Jul. 24, 2014

(65) Prior Publication Data
US 2015/0351392 A1 Dec. 10, 2015

Related U.S. Application Data

(60) Provisional application No. 61/753,000, filed on Jan. 16, 2013.

(51) Int. Cl.
| *A01G 24/00* | (2018.01) |
| *A01N 43/16* | (2006.01) |
| *A01N 61/00* | (2006.01) |
| *A01G 22/00* | (2018.01) |

(52) U.S. Cl.
CPC ............. *A01N 43/16* (2013.01); *A01G 22/00* (2018.02); *A01G 24/00* (2018.02); *A01N 61/00* (2013.01)

(58) Field of Classification Search
CPC ........ A01G 1/001; A01G 7/00; A01G 9/1086; A01G 24/00
USPC ............................... 47/48.5, 58.1 R, 58.1 SC
See application file for complete search history.

(56) References Cited

U.S. PATENT DOCUMENTS

| 4,487,766 A | 12/1984 | Mach | |
| 4,952,229 A * | 8/1990 | Muir | A01G 13/0262 47/58.1 R |
| 5,155,931 A * | 10/1992 | Vansteenkiste | A01G 31/001 47/41.12 |
| 6,174,712 B1 * | 1/2001 | Yokoyama | A01N 37/36 435/132 |
| 7,060,656 B2 * | 6/2006 | Kato | A01G 31/001 424/409 |
| 7,347,150 B2 * | 3/2008 | Shu | A01G 1/005 111/199 |
| 2004/0139653 A1 * | 7/2004 | Morelle et al. | A01G 31/00 47/59 S |
| 2010/0058661 A1 * | 3/2010 | Jackson | A01G 31/001 47/59 S |
| 2010/0255124 A1 * | 10/2010 | Green | A01N 27/00 424/725 |

FOREIGN PATENT DOCUMENTS

| CN | 101668417 A | 3/2010 |
| CN | 102823918 A | 12/2012 |
| WO | WO 01/07380 A1 | 2/2001 |

OTHER PUBLICATIONS

Cui, C. et al., "Research Progress of Melanoidins", Food Science, Dec. 2007, pp. 1-26, vol. 28, No. 8 (with English abstract).
Coghe, S. et al., "Fractionation of Colored Maillard Reaction Products from Dark Specialty Malts", Journal of American Society of Brewing Chemists, American Society of Brewing Chemists, St Paul, MN, US, Jan. 1, 2004 (Jan. 1, 2004), pp. 79-86, vol. 62, XP009190557.
Database FSTA [Online] International Food Information Service (IFIS), Frankfurt-Main, DE; Jan. 1, 1990 (Jan. 1, 1990), Grechko N Ya et al., "Formation of colorants in dried malt and ferment concentrate. (translated)," 1 page, XP002758812.
Kamei, H. et al., "Tumor Cell Growth-Inhibiting Effect of Melanoidins Extracted from Miso and Soy Sauce," Cancer Biotherapy & Radiopharmaceuticals, Dec. 31, 1997, pp. 405-409, vol. 12, No. 6.
Khripovich, A. A., "Effect of Copper Chloride on the Maillard Reaction in Acidic Medium", Vestsi akad., Belarusi, Dec. 31, 2001, pp. 82-85, vol. 2.

(Continued)

*Primary Examiner* — David J Parsley
(74) *Attorney, Agent, or Firm* — Fenwick & West LLP

(57) ABSTRACT

The present invention relates to melanoidins and their use for improving properties of plants. The methods and compositions of the invention are particularly useful for control of fungal plant diseases and drought conditions, and promotion of plant growth.

25 Claims, 16 Drawing Sheets

(56) References Cited

OTHER PUBLICATIONS

Khripovich, A. A. et al., "Chemical Composition of Aminogumat, a Plant Growth Regulator" In: "Khimiya Tverdogo Topliva", Jan. 1, 2003 (Jan. 1, 2003), Caplus Database 141: 135627, pp. 3-8, vol. 5, XP055280702.

Mahamoudi, H. et al., "Varied Tolerance to NaCl Salinity is Related to Biochemical Changes in Two Contrasting Lettuce Genotypes," Acta Phsysiologiac Plantarum, Sep. 30, 2011, pp. 1613-1622, vol. 33, No. 5.

Moreira, A. S. P. et al., "Coffee Melanoidins: Structures, Mechanisms of Formation and Potential Health Impacts", Food & Function, Jan. 1, 2012 (Jan. 1, 2012), pp. 903-915, vol. 3, No. 9, XP055280679.

Murugaragavan, R et al., "Characterization of Distillery Spentwash for its Valuable Nutrient Substitute to Dryland Agriculture", Journal of Ecobiology, Palany Paramount Publ, Jan. 1, 2009 (Jan. 1, 2009), pp. 169-174, vol. 24, No. 2, XP009190566.

Posadino, A. M. et al., "Prune Melanoidins Protect Against Oxidative Stress and Endothelial Cell Death," Frontiers in Bioscience, E3, Jun. 1, 2011, pp. 1032-1041.

Rivero, D. at al., "Inhibition of Induced DNA Oxidative Damage by Beers: Correlation with the Content of Polyphenols and Melanoidins," Journal of Agricultural and Food Chemistry, May 1, 2005 (May 1, 2005), pp. 3637-3642, vol. 53, No. 9, XP055280588, US.

Rurian-Henares, J. A. et al., "Antimicrobial Activity of Melanoidins Against *Escherichia coli* is Mediated by a Membrane-Damage Mechanism," Journal of Agriculture and Food Chemistry, Dec. 31, 2008, pp. 2357-2362, vol. 56.

Shin, J.-H. et al., "Rice Aldehyde Dehydrogenase7 is Needed for Seed Maturation and Viability", Plant Physiology, Feb. 28, 2009, pp. 905-915, vol. 149.

Stecchini, M. L. et al., "Effect of Maillard Reaction Products on the Growth of Selected Food-Poisoning Micro-Organisms", Letters in Applied Microbiology, Jan. 1, 1991 (Jan. 1, 1991), pp. 93-96, XP055280685.

Walker, J. R.L. et al., "Dephenol Oxidases, Enzyme-Catalysed Browning and Plant Disease Resistance", Biotechnology and Genetic Engineering Reviews, Apr. 30, 1998, pp. 457-498, vol. 15, No. 1.

Woffenden, H. M. et al., "Relationships between Antioxidant Activity, Color, and Flavor Compounds of Crystal Malt Extracts," Journal of Agricultural and Food Chemistry, Nov. 1, 2001 (Nov. 1, 2001), pp. 5524-5530, vol. 49, No. 11, XP055280838.

European Extended Search Report, European Application No. 1474080039, dated Jun. 27, 2016, 14 pages.

Chinese Office Action, Chinese Application No. 201480008972.3, dated Aug. 4, 2016, 13 pages.

PCT International Search Report, PCT Application No. PCT/IL2014/050047, dated Mar. 13, 2014, 4 pages.

PCT Written Opinion, PCT Application No. PCT/IL2014/050047, dated Mar. 13, 2014, 5 pages.

European Examination Report, European Application No. 14740800.9, dated Jun. 2, 2017, 15 pages.

Kim, J-S. et al., "Enolization and Racemization Reactions of Glucose and Fructose on Heating with Amino-Acid Enantiomers and the Formation of Melanoidins as a Result of the Maillard Reaction," Amino Acids; The Forum for Amino Acid and Protein Research, Springer-Verlag, May 22, 2008, pp. 465-474, vol. 36, No. 3.

\* cited by examiner

MELANOIDINS AND THEIR USE FOR IMPROVING PROPERTIES OF PLANTS

FIELD OF THE INVENTION

This invention relates to melanoidins and their use for improving properties of plants. Specifically, the invention relates to methods and compositions comprising melanoidins for controlling fungal plant diseases, inducing plant tolerance to drought conditions and promoting plant growth.

BACKGROUND OF THE INVENTION

Melanoidins are polymeric and colored final products of the Maillard reaction, or "nonenzymatic browning reaction" consisting of a series of complex reactions that occurs during the heating of reducing sugars or carbohydrates together with amines, amino acids or proteins. Melanoidins are the compounds responsible for the brown color of roasted, baked, toasted, grilled, charred or browned foods, and are also common in many dietary liquids such as soy sauce, honey, wine, beer and coffee. Melanoidins are formed by cyclizations, dehydrations, retroaldolisations, rearrangements, isomerisations, and condensations that occur over the course of the Maillard reaction [Wang, H-Y, Qian, H, Yao, W-R. Food Chemistry, 2011, 128:573-584].

The structure of melanoidins is poorly defined, as these heterogeneous macromolecular compounds cannot be individually characterized. Three major proposals for their structure have been advanced: (i) polymers consisting of repeating units of furans and/or pyrroles, linked by polycondensation reactions; (ii) low-molecular-weight (LMW) colored substances cross-linked with proteins via s-amino groups, giving high molecular weight (HMW) colored melanoidins; and (iii) skeletons built up of sugar degradation products formed in the early stages of the Maillard reaction, polymerized through aldol-type condensation, and linked by amino compounds [Wang, H-Y, Qian, H, Yao, W-R. Food Chemistry, 2011, 128:573-584].

Being virtually ubiquitous in many food stuffs, there is interest in exploring the dietary function of melanoidins. They have been found to have a host of in vitro and in vivo functional properties, including: (i) free radical scavenging and antioxidant activity; (ii) anti-microbial activity; (iii) metal chelating ability; (iv) anti-microbial adhesion and anti-biofilm forming action; (v) lipid peroxidation inhibition; and (vi) inhibitory or promoting effects on activities of various enzymes.

Besides being ubiquitous in food stuffs, melanoidins have long been believed to be amongst the building blocks of humic substances, the brown colored macromolecular materials making up much of the natural organic matter in soil. Water soluble humic substances (humic and fulvic acids) are also an important part of the organic matter in aqueous environments and in atmospheric aerosol. Like humic and fulvic acids, melanoidins exert a partially anionic character in aqueous solution over a wide pH range. They can be separated into size fractions using dialysis, ultrafiltration or gel permeation techniques, with an arbitrary operational molecular weight cutoff of 10,000 or 12,400 Daltons for distinguishing between high molecular weight (HMW) and low molecular weight (LMW) melanoidins. Solubility of HMW melanoidins is enhanced at high pHs. At very low pH, the darker brown HMW melanoidins precipitate, while the LMW light straw colored melanoidins remain in solution. HMW melanoidins can also be flocculated by multivalent inorganic cations. Compared with humic substances, melanoidins are considerably more water soluble and have a much greater N content as a result of their derivation from amino acids.

Humic substances have been long reported to have positive effects on plant nutrition, seed germination, root initiation, and total plant biomass. For example, the ability of humic substances to chelate important plant micronutrients (Fe and Zn) and enhance their solubility in nutrient solution was found to enhance the growth of melons, soybean, and ryegrass. Humic acid was also found to have a transient effect on the transcriptional regulation of principal molecular agents involved in iron assimilation in non-Fe deficient cucumber plants. Humic acids, and particularly, low molecular weight humic acids, were found to increase the rate of nitrate uptake in wheat plants, apparently via the promotion of the molecular expression of proteins participating in nitrate support systems. In cucumber, humic acid application was associated with enhanced root H+-ATPase activity, increased nitrate shoot concentration, and decreased root nitrate concentration, effects accompanied by concomitant increases and decreases in several cytokinins and polyamines. Humic acids were reported to induce a partial relief from P starvation in tobacco BY-2 suspension cell cultures, increasing total cell phosphate amount, ATP and glucose-6-phosphate levels, and the activity of secreted acid phosphatases. Humic acid was also observed to impact root plasma membrane H+-ATPase activity and expression in maize, resulting in root growth promotion and proton pump activation, possibly due to the release of auxin-like plant growth promoters from the humic acids. Other evidence for auxin-like activity of humic substances is activation of the auxin synthetic reporter (DR5::GUS) and subsequent enhanced transcription of the early auxin responsive gene IAA19 in *Arabidopsis*, inducing lateral root formation.

No information is available regarding the effects of melanoidins on growth or functioning of plants.

Powdery mildew and Gray mold are two examples of fungal promoted diseases in plants. Said diseases are widespread and easily recognizable, causing serious damage to a wide range of plants, trees and agriculturally crops.

Powdery mildew is caused by plant pathogens (e.g., *Oidium neolycopersici*, an obligate parasite, i.e., the parasite attacks and can live only on living host tissues). Germination and infection are favored by fairly high humidity conditions. The fungus spreads very quickly in terms of a few days only. The conidia spread over short distances by wind and rain. The powdery mildew fungus grows on the surface of plant tissues. It penetrates the leaf surface with specialized cells called haustoria which gather nutrients and energy from the host leaf. Conidia are produced on the leaf surface within as little as 60 hours after initial infection and are carried by air currents to another leaf which they can directly infect by germinating.

*Botrytis cinerea* is another type of fungal pathogen which causes a widespread plant disease, damaging plants including agriculturally important crops, such as tomatoes and cucumbers. *B. cinerea* is the causal agent of gray-mold. Germination and infection of *B. cinerea* are favored by fairly high humidity and relatively cool conditions. Under these conditions, germination and infection can take place in a few hours.

Generally, when disease is severe, as it may be on tomato, cucumber or other crops, fungicidal sprays may be used to protect nearby healthy plants.

Typically, avoiding conditions of high humidity is the most effective way currently available to reduce the likelihood of spreading the diseases. However, there is no effective solution for controlling the diseases in affected plants once the disease is established.

Drought is one of the stresses that plants face while growing. Drought may be caused by limited availability of water or the inability of plants to absorb and transfer water to the canopy because of disturbed plant water relations and reduced water-use efficiency. It may also be caused by high temperatures or high vapor pressure deficit. Morphologically, plant reactions to drought conditions include reduced growth, for instance, as observed in plant height, leaf size and stem width. Under severe drought conditions, plants will wilt. In cases of severe wilt, leaves may not recover from the stress once plants are irrigated again, and the wilt thus results in death of leaves and other plant organs.

It has now been surprisingly found that melanoidins obtained from the Maillard reaction are active agents that can substantially improve plant properties.

It is therefore an object of the present invention to provide melanoidins and compositions comprising thereof that can be used for promoting plant well-being.

It is another object of the invention to provide melanoidins and compositions comprising thereof for use in controlling plant diseases.

It is still another object of the invention to provide melanoidins and compositions comprising thereof for use in protecting plants under drought conditions.

It is a further object of the invention to provide melanoidins and compositions comprising thereof for use in promoting plant growth.

SUMMARY OF THE INVENTION

According to a first aspect, the invention relates to a composition comprising melanoidins for improving plant properties, wherein said melanoidin is a product of the Maillard reaction. The melanoidin is prepared from any combination of one or more amino acid and/or protein and one or more reducing sugar or carbohydrates containing reducing sugars.

According to one specific embodiment, the invention provides a composition for improving plant resistance to plant fungal pathogens. According to another specific embodiment, the invention provides a composition for improving drought tolerance of plants. According to a further specific embodiment, the invention provides a composition for improving plant growth.

In some embodiments of the invention, the melanoidin is present at a concentration range of $10^{-5}$-5% w/v. In other embodiments of the invention the melanoidin is present at a concentration range of 0.001-0.1% w/v.

It should be noted that compositions of the invention are adapted for application by spray, drench, irrigation, or fertigation.

The plants to be treated according to the invention belong to the Solanceae family or the Cucurbitaceae family. According to one specific embodiment, the pathogen combated according to the invention is a powdery mildew pathogen or a gray mold pathogen. According to another specific embodiment, the fungal pathogen is selected from *Oidium neolycopersici, Podosphaera xanthii* and *Botrytis cinerea*.

According to a second aspect, the invention relates to a method for improving plant properties, comprising applying to the plant or a portion thereof an effective amount of a composition comprising melanoidin, wherein said melanoidin is a product of the Maillard reaction.

According to one specific embodiment, the invention provides a method for improving plant resistance to plant diseases caused by fungal pathogens. According to another specific embodiment, the invention provides a method for improving drought tolerance of plants. According to a further specific embodiment, the invention provides a method for improving plant growth.

In one embodiment of the method of the invention, the melanoidin is applied to a plant once. In a different embodiment of the method of the invention the melanoidin is applied at least twice on different days. In another embodiment of the method of the invention the melanoidins is applied with the irrigation or fertigation water.

It should be noted that the melanoidin according to the invention is applied to any plant organ at any stage of its life cycle.

All the above and other characteristics and advantages of the invention will be further understood through the following illustrative and non-limitative description of embodiments thereof, with reference to the appended drawings. In the drawings the same numerals are sometimes used to indicate the same elements in different drawings.

Abbreviations: C (control).

Figure 2A:
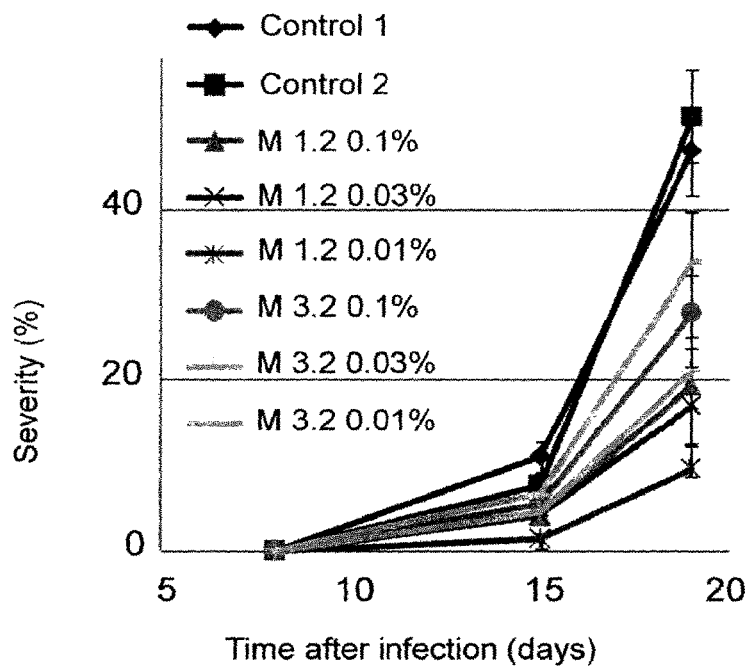
Figure 2B:
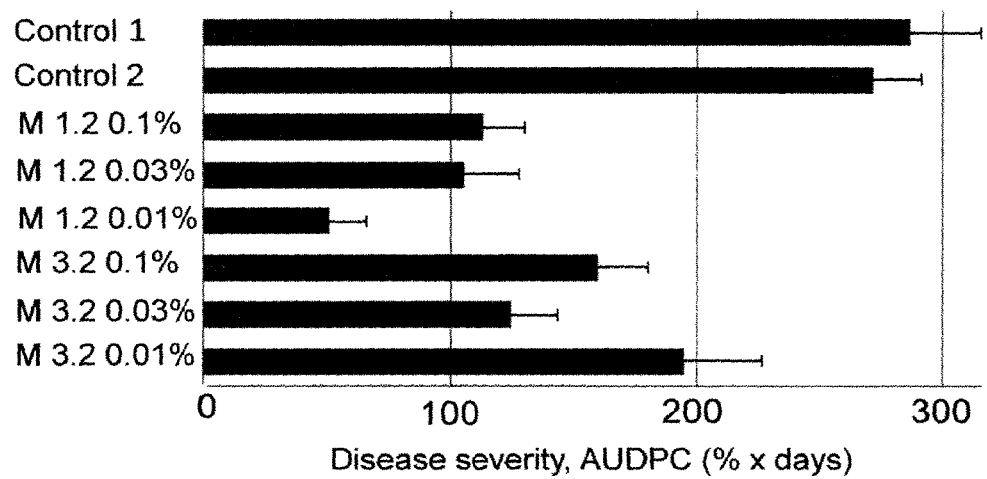

FIG. 2A-2B show the effect of different melanoidins (3 batches of M1 and 3 batches of M3) on the severity of powdery mildew (*Oidium neolycopersici*) in tomato. Bars represent standard error.

FIG. 2A demonstrates the effect of melanoidins at different days after infection. Disease severity is presented as % of infected area.

FIG. 2B demonstrates the effect of melanoidins over the course of 19 days after infection. Disease severity is presented as area under disease progress curve (AUDPC). Bars represent standard error.

FIG. 3A-3D show the effect of different melanoidins on the severity of powdery mildew (*O. neolycopersici*) in tomato plants.

Figure 3B:
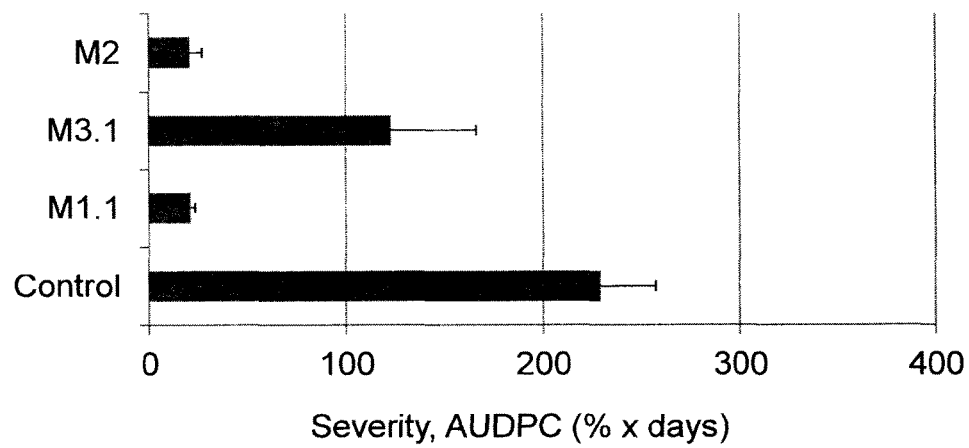
Figure 3A:
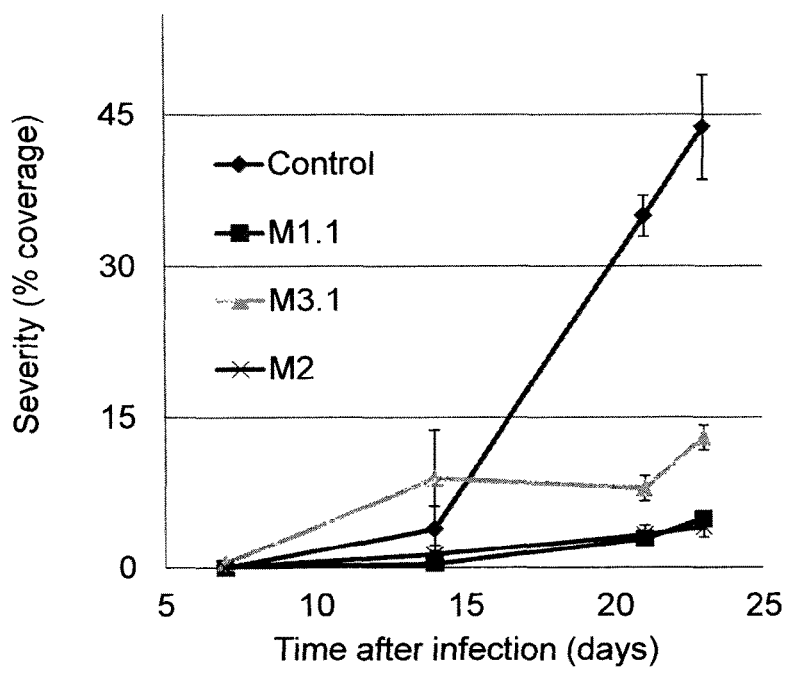

FIG. 3A demonstrates the effect of melanoidins application by spray at different days after infection. Disease severity is presented as % of infected area. Bars represent standard error.

FIG. 3B demonstrates the effect of melanoidins application by spray over the course of 23 days after infection. Disease severity is presented as area under disease progress curve (AUDPC). Bars represent standard error.

Figure 3D:
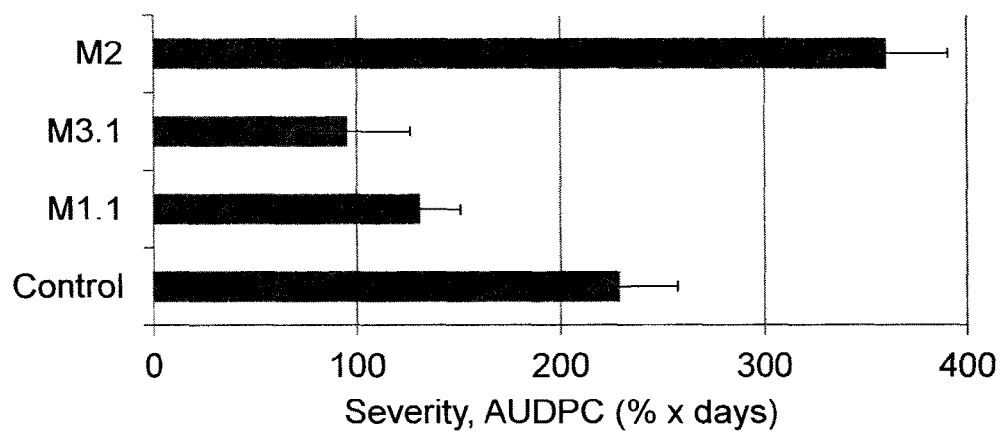
Figure 3C:
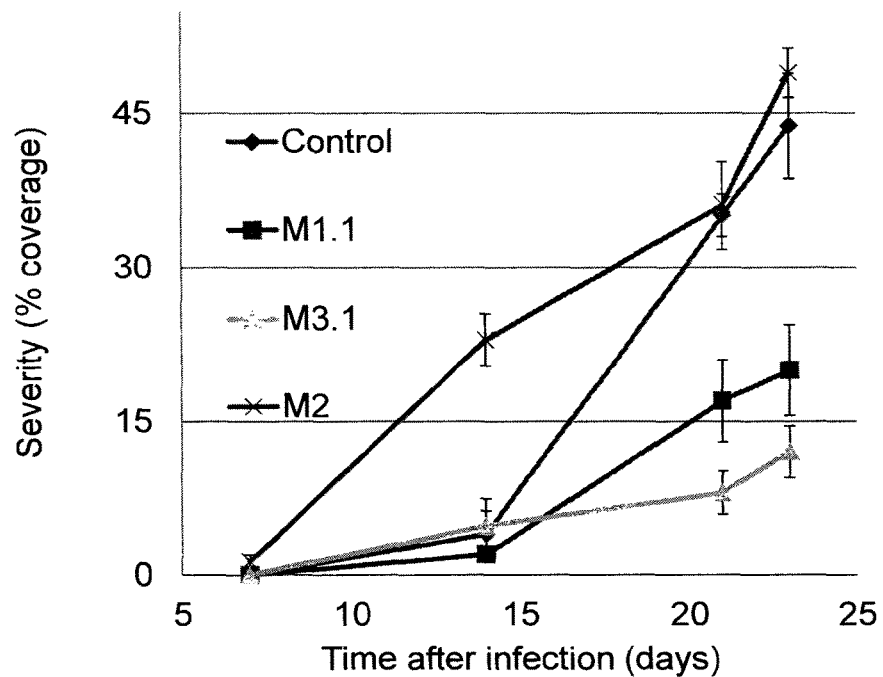

FIG. 3C demonstrates the effect of melanoidins application by drench at different days after infection. Disease severity is presented as % of infected area. Bars represent standard error.

FIG. 3D demonstrates the effect of melanoidins application by drench over the course of 23 days after infection. Disease severity is presented as % of infected area and as area under disease progress curve (AUDPC). Bars represent standard error.

Figure 4A:
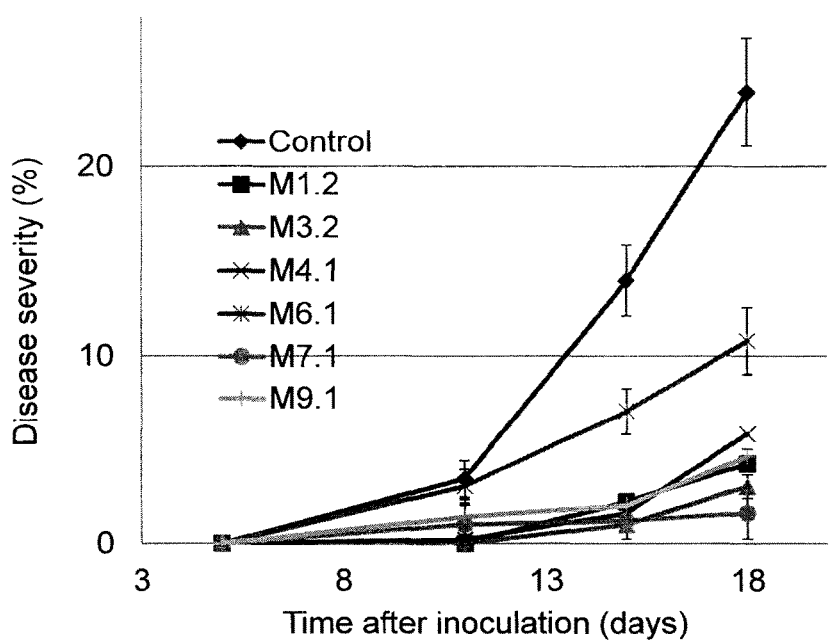
Figure 4B:
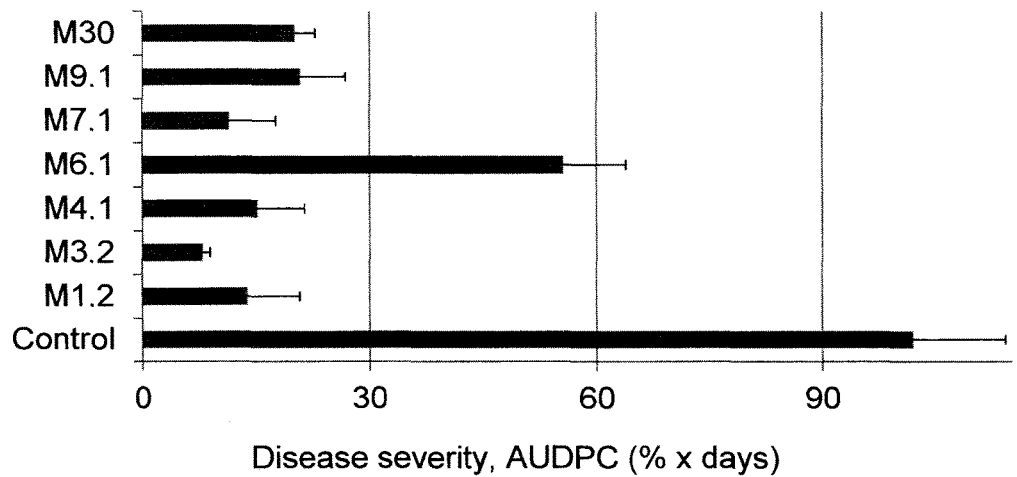

FIG. 4A-4B show the effect of spray of solutions of different melanoidins on powdery mildew (*O. neolycopersici*) severity in tomato.

FIG. 4A demonstrates the effect of melanoidins at different days after infection. Disease severity is presented as % of infected area. Bars represent standard error.

FIG. 4B demonstrates the effect of melanoidins over the course of 23 days after infection. Disease severity is presented as % of infected area and as area under disease progress curve (AUDPC). Bars represent standard error.

Figure 5:
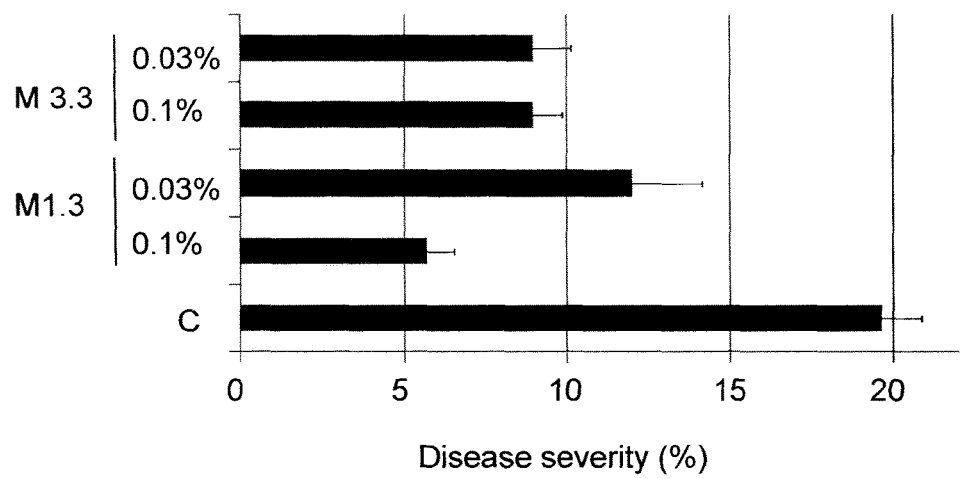

FIG. 5 shows the effect of solutions of different melanoidins on the disease severity of well-established powdery mildew (*O. neolycopersici*) 42 days after treatment. Disease severity is presented as % of infected area. Bars represent standard error.

Figure 6:
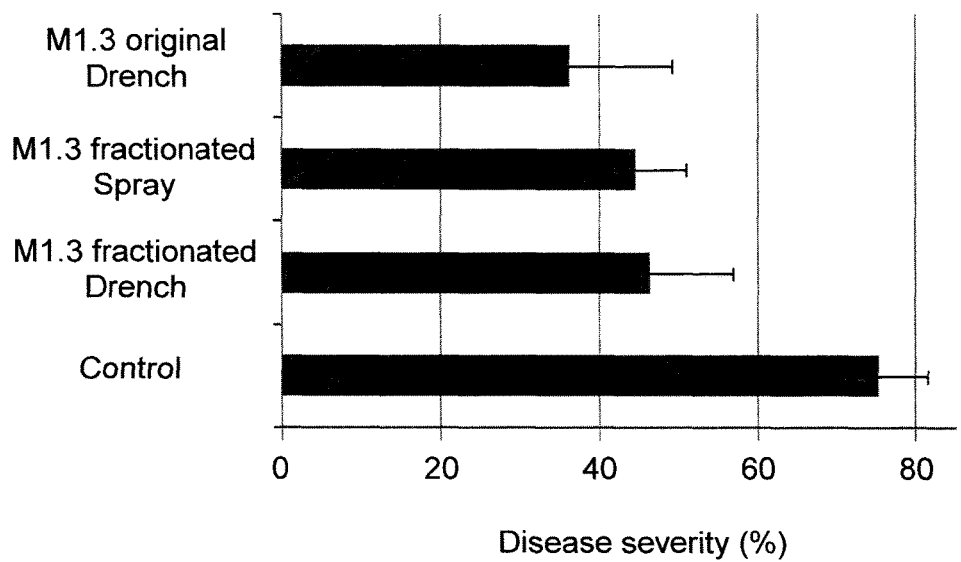

FIG. 6 shows the effect of ultrafiltration of melanoidins (M1.3) into high molecular weight (HMW) fraction of melanoidins and non-fractionated melanoidins on the severity of gray mold (*B. cinerea*) in tomato. Application of HMW fraction or unfractionated solution was carried out by drench and by spray. Disease severity was evaluated 7 days after infection as % of infected area. Bars represent standard error.

Figure 7A:
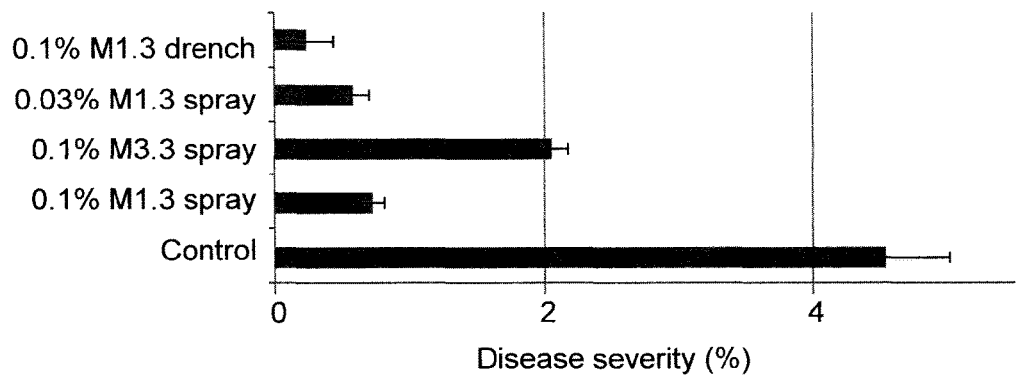
Figure 7B:
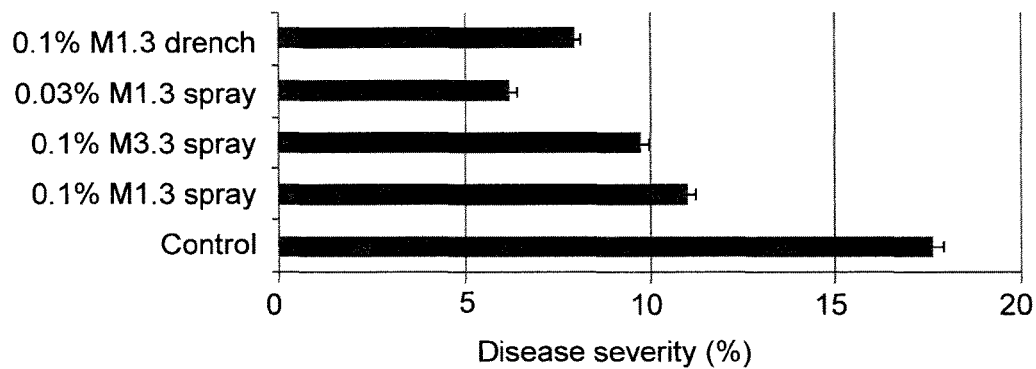
Figure 7C:
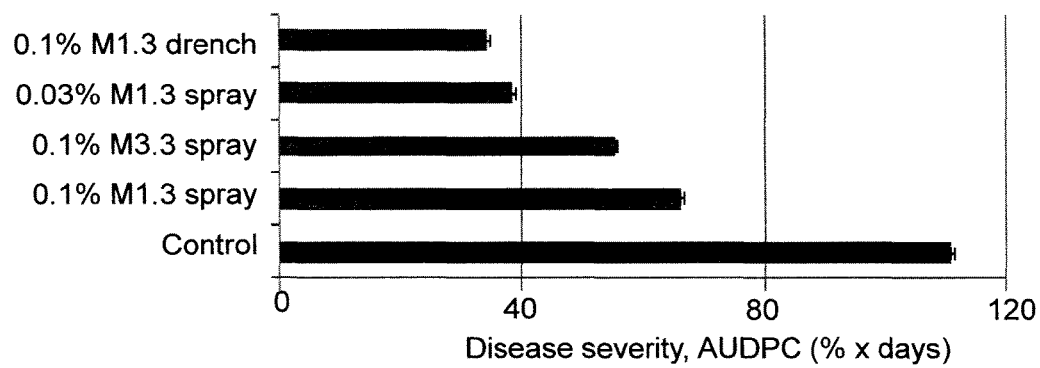

FIG. 7A-7C show the effect of drench and spray of solutions of different melanoidins on severity of powdery mildew (*Podosphaera xanthii*) in cucumber. Disease severity is presented as % of infected area 12 days after infection (A) and 23 days after infection (B) and as area under disease progress curve (AUDPC) over the course of 23 days (C). Bars represent standard error.

Figure 8A:
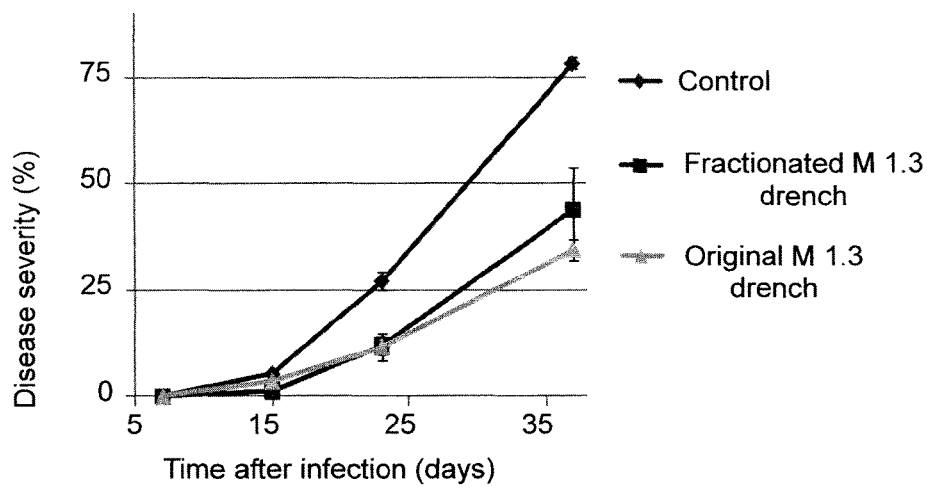
Figure 8B:
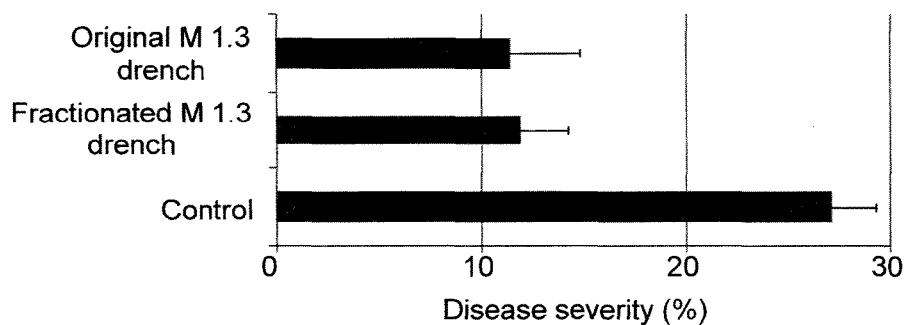
Figure 8C:
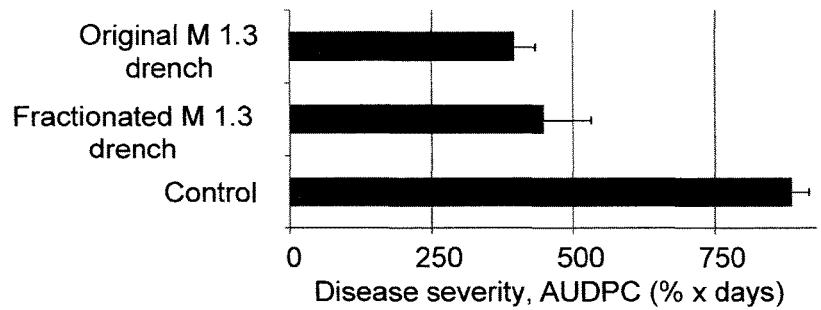

FIG. 8A-8C show the effect of 0.03% of ultrafiltration of melanoidins into high molecular weight (HMW) fraction of melanoidins (denoted "fractionated") and non-fractionated (denoted "original") melanoidins applied by drench on severity of cucumber powdery mildew (*P. xanthii*).

FIG. 8A demonstrates the effect of melanoidins at different days after infection. Disease severity is presented as % of infected area. Bars represent standard error.

FIG. 8B demonstrates the effect of melanoidins on day 23 after infection. Disease severity is presented as % of infected area. Bars represent standard error.

FIG. 8C demonstrates the effect of melanoidins on day over the course of 36 days after infection. Disease severity is presented as % of infected area and as area under disease progress curve (AUDPC). Bars represent standard error.

Figure 9:
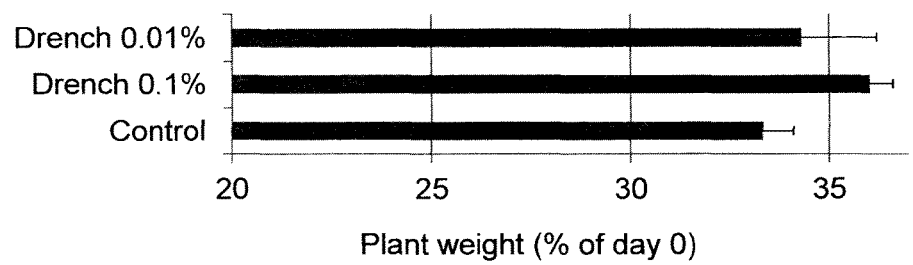

FIG. 9 shows the effect of drench of melanoidin solutions on plant weight 3 weeks after last irrigation. Plant weight is presented as percent of original weight (day 0). Bars represent standard error.

Figure 10:
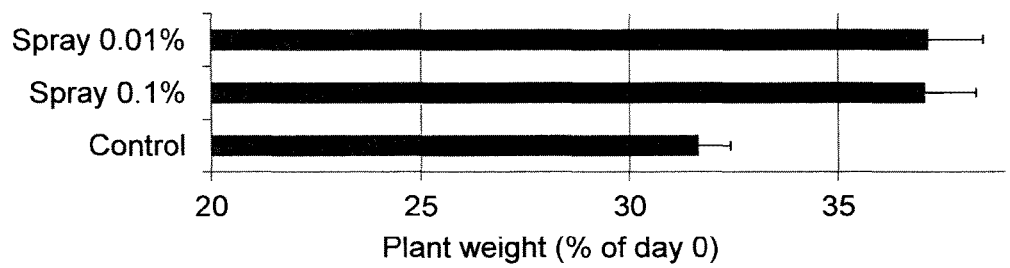

FIG. 10 shows the effect of spray of melanoidin solutions on plant weight 3 weeks after last irrigation. Plant weight is presented as percent of original weight (day 0). Bars represent standard error.

Figure 11:
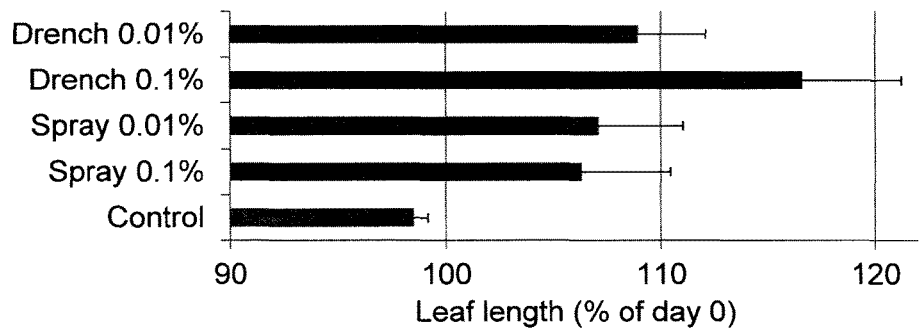

FIG. 11 shows the effect of drench and spray of melanoidin solutions on leaf length 2 weeks after last irrigation. Leaf length is presented as percent of original weight (day 0). Bars represent standard error.

Figure 12:
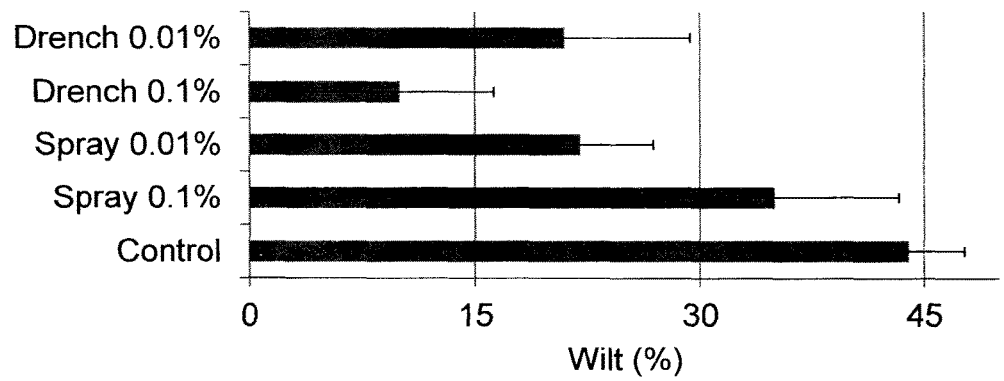

FIG. 12 shows the effect of drench and spray of melanoidin solutions on the wilt severity at 4 hours after irrigation that followed 3 weeks of no irrigation. Wilt is presented as percent. Bars represent standard error.

Figure 13:

FIG. 13 shows the effect of drench and spray of melanoidin solutions on the number of live leaves per plant at 4 hours after irrigation that followed 3 weeks of no irrigation. Wilt is presented as percent. Bars represent standard error.

Figure 14A:
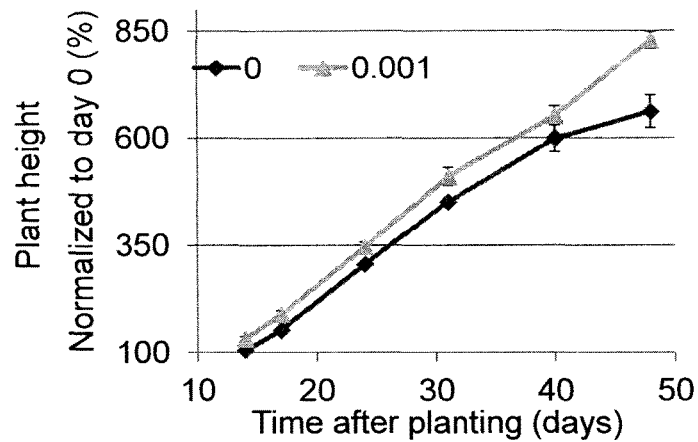
Figure 14B:
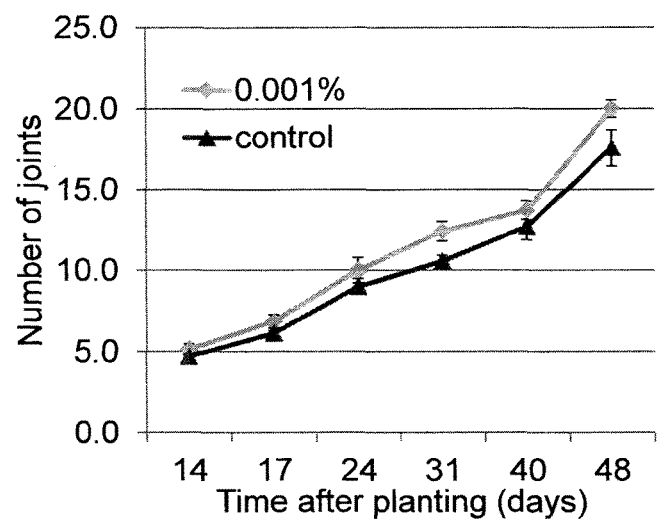
Figure 14C:
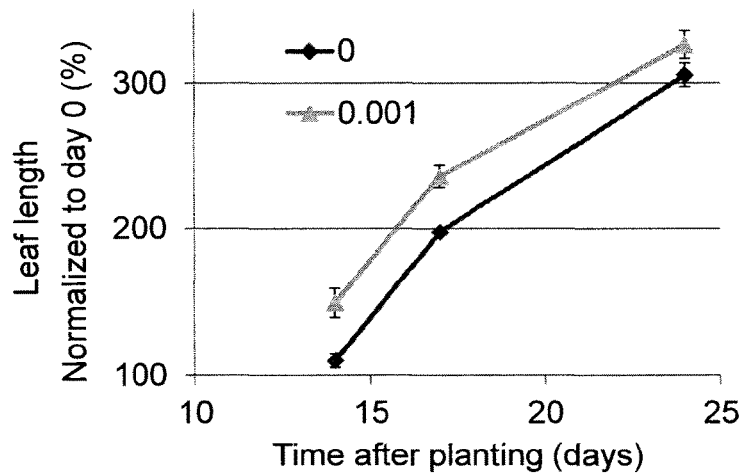

FIG. 14A-14C show the effect of melanoidins applied in fertigation solution on tomato plant growth over 48 days following transplanting. Bars represent standard error.

FIG. 14A: Normalized plant height

FIG. 14B: Number of stem joints

FIG. 14C: Leaf length.

Figure 15:
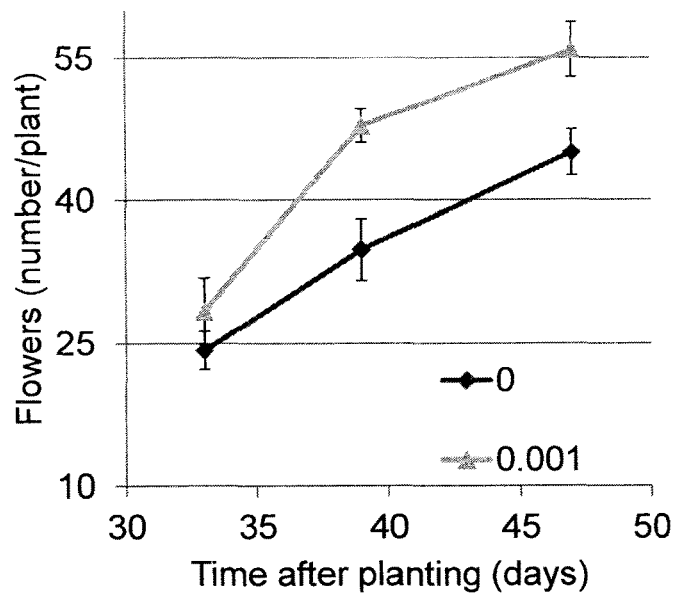

FIG. 15 shows the effect of melanoidins applied in fertigation solution on number of tomato flowers per plant over time. Bars represent standard error.

Figure 16A:
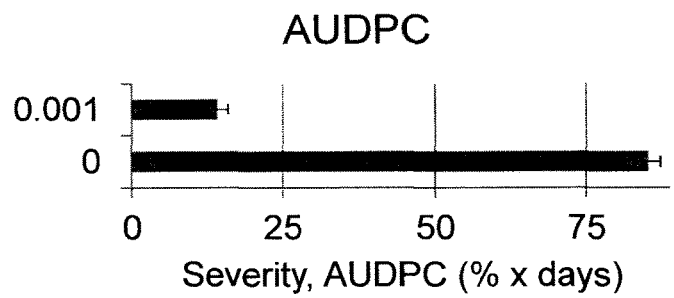
Figure 16B:
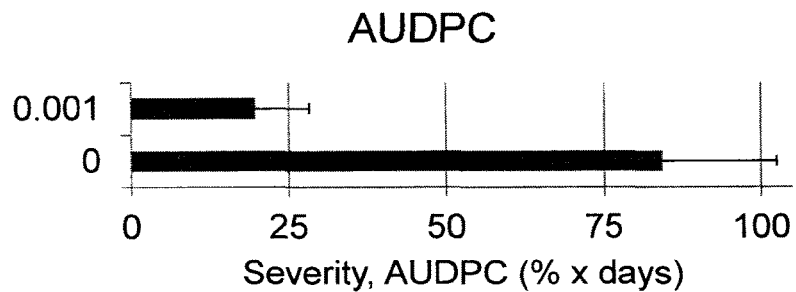

FIG. 16A-16B show the effect of melanoidins applied in fertigation solution on *B. cinerea* severity in terms of area under the disease progress curve (AUDCP) on detached tomato leaves 4 weeks after transplanting (FIG. 16A) and eight weeks after transplanting (FIG. 16B). Bars represent standard error.

Figure 17:
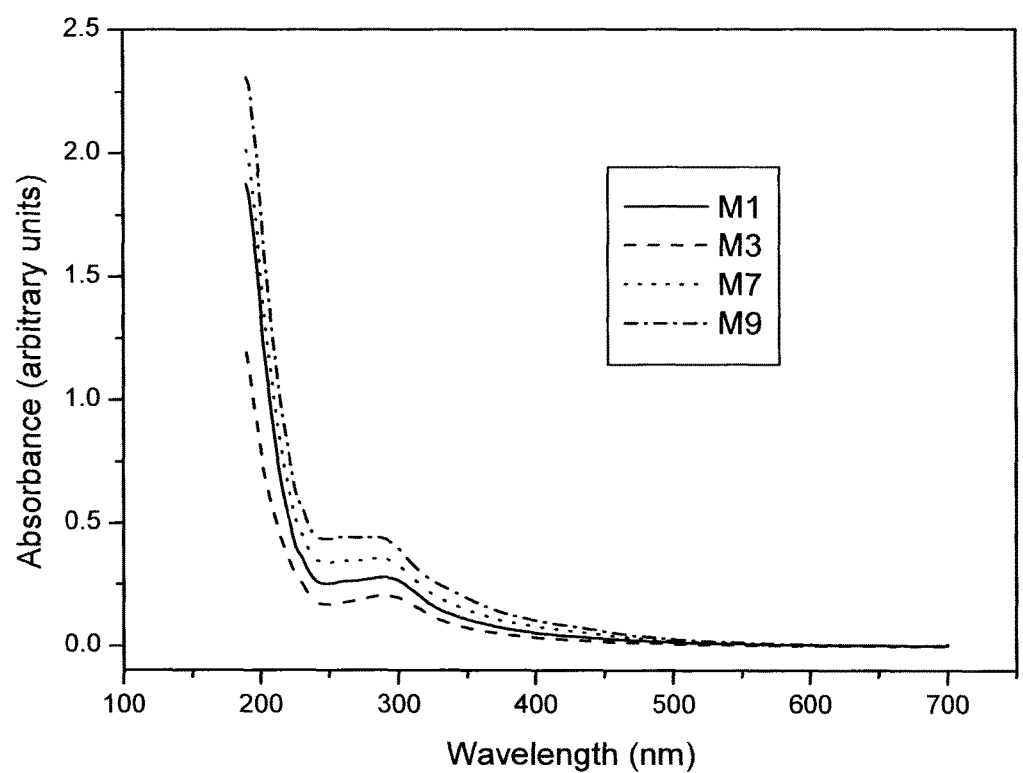

FIG. 17 shows the UV-Vis scan of different melanoidins formulations. The measurements were performed on a UV-Vis spectrophotometer ThermoScientific (Genesys 10 UV) between 190 to 700 nm.

FIG. 18A-18D show the fluorescence excitation-emission spectra of different melanoidins formulations.

Figure 18A:
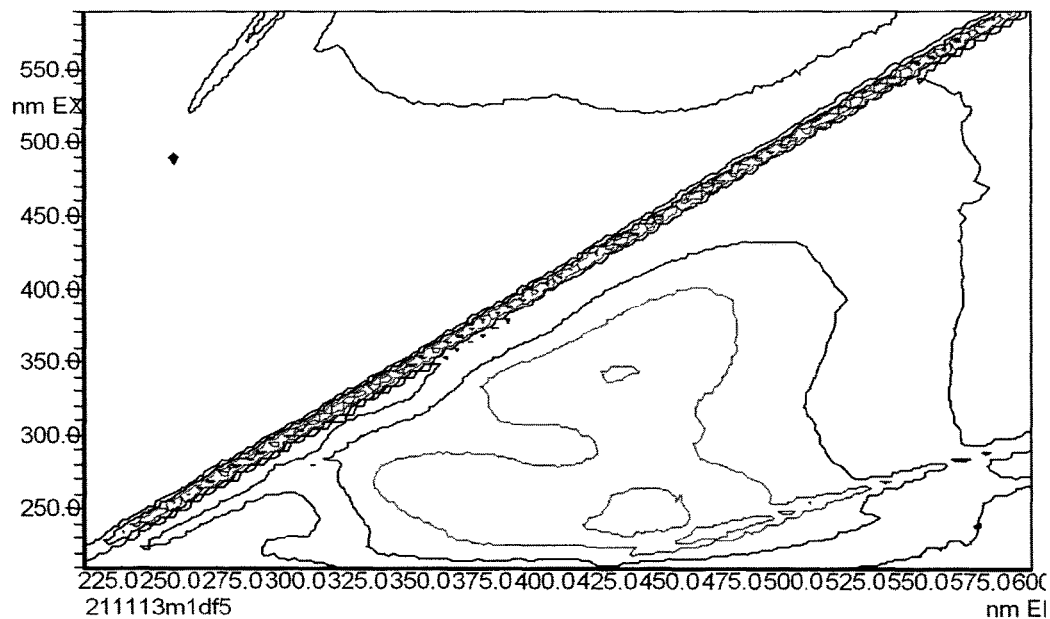

FIG. 18A: fluorescence excitation-emission spectra of M1.

Figure 18B:
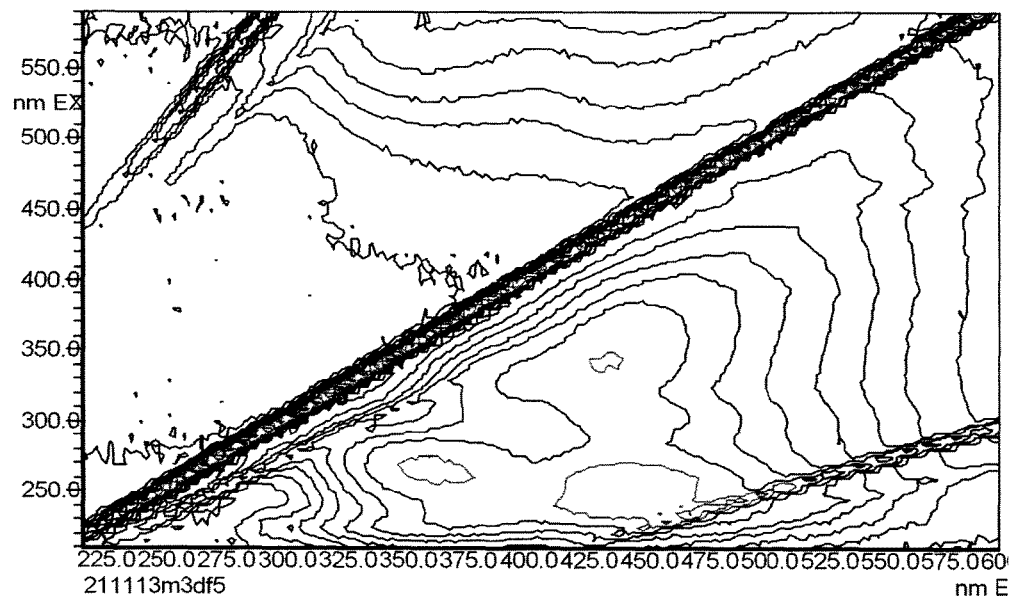

FIG. 18B: fluorescence excitation-emission spectra of M3.

Figure 18C:
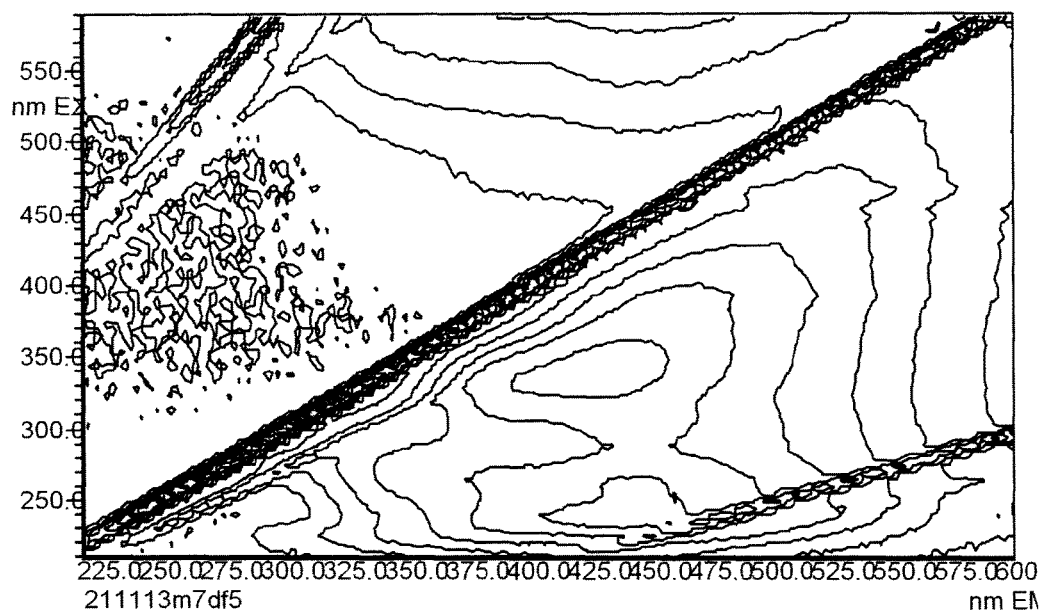

FIG. 18C: fluorescence excitation-emission spectra of M7.

Figure 18D:
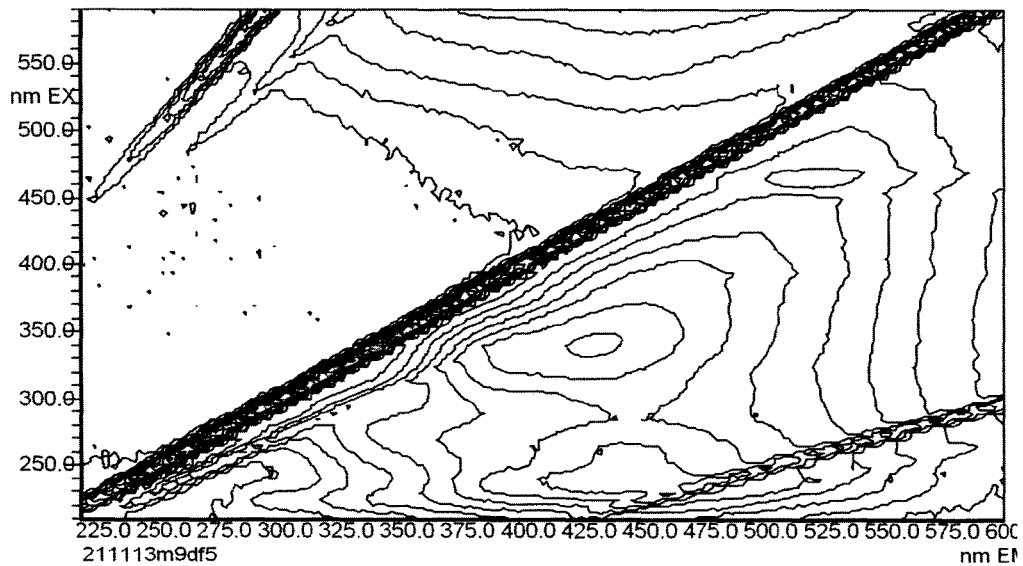

FIG. 18D: fluorescence excitation-emission spectra of M9.

Figure 19:
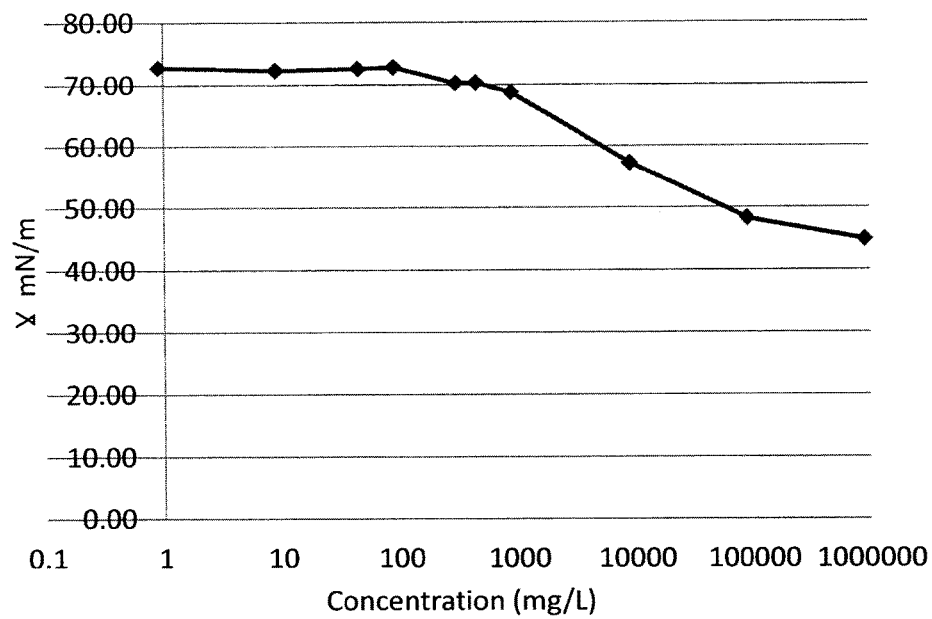

FIG. 19 shows the surface tension (mN/m) of M1 aqueous solutions as a function of concentration.

Figure 20:
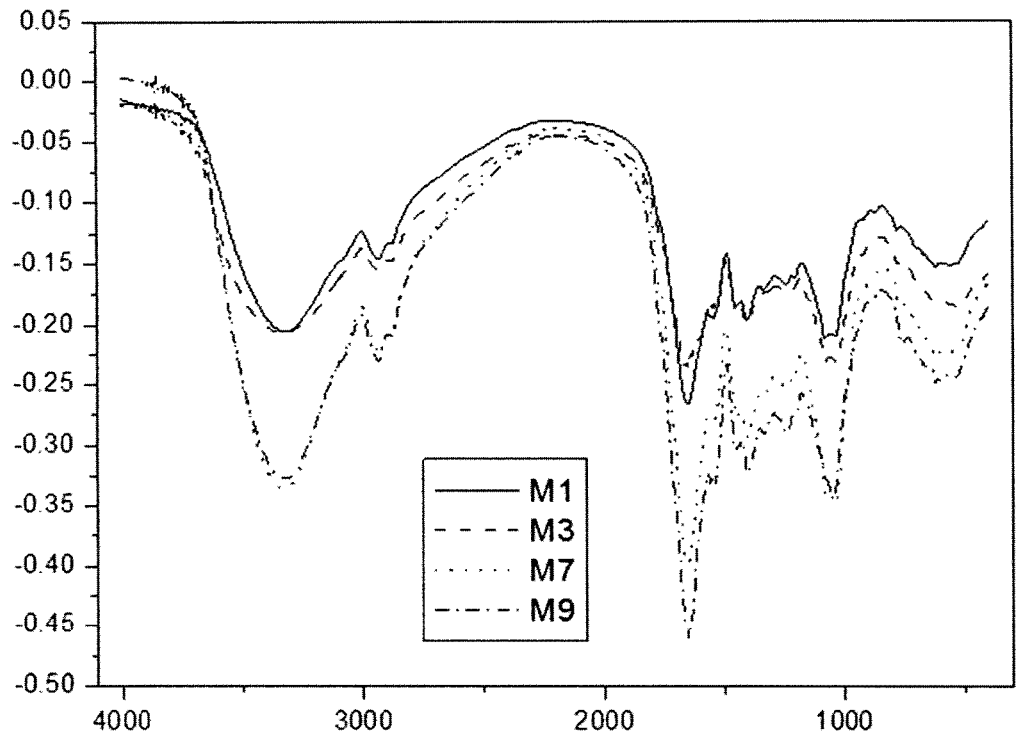

FIG. 20 shows the FTIR transmission spectra for various melanoidins formulations (M1, M3, M7, and M9).

DETAILED DESCRIPTION OF THE INVENTION

The disclosed invention provides a method and composition useful for improving plant properties. The method and composition are specifically useful in preventing and controlling plant diseases caused by fungal pathogens (e.g. foliar fungal pathogens), for protecting plants from draught conditions and for promoting and improving plant growth. The composition comprises melanoidins, and can be applied by spray, drench, irrigation, fertigation, or any other way of application.

The terms "properties of a plant" or "plant properties" relate to growth, development, and/or robustness of a plant. Growth refers to an increase in size, development refers to the process of going through developmental stages (e.g., germinating, budding, flowering, etc.), and robustness refers to ability of the plant to withstand either or both abiotic and biotic stresses. Abiotic stresses involve environmental conditions such as but not limited to temperature and drought. Biotic stresses involve pests (e.g., insects, worms or parasitic plants, etc.) and pathogens (e.g., fungi, bacteria, viruses, etc.).

The term "improving plant properties" relates to any characteristic of a plant that is advanced to a more desirable and/or valuable state, for example, improved growth and development, enhanced resistance to pathogens, better tolerance to abiotic stresses such as drought and temperature.

The term "plant disease" refers to diseases caused by both abiotic and biotic stresses.

The term "controlling a plant disease" relates to a reduction in disease severity, incidence, or symptoms on the host plant. The term also encompasses suppressing the causative agent of the disease, e.g. fungal pathogen.

The term "drought conditions" relates to drought stress that reduces plant growth in terms of leaf size, stem extension and root proliferation, disturbs plant water relations and reduces water-use efficiency. Drought stress results when water loss from the plant exceeds the ability of the plant's roots to absorb water and when the plant's water content is reduced enough to interfere with normal plant processes. Accordingly, the terms "protecting plants from drought conditions" or "inducing plant drought tolerance" relate to a reduction in plant reactions to water supply deficiency and to stress imposed by increased water loss.

Plant growth is defined as the process by which a plant increases in the number and size of leaves and stems. The term "promoting plant growth" relates to the stimulation of increased development of the plant in general, or any organ thereof, including leaf, stem, root, flower, and fruit.

It should be noted that in this specification and the appended claims, the singular form "melanoidin" also includes any combination of two or more melanoidins.

Melanoidins are polymeric and colored final products of the Maillard reaction, or "nonenzymatic browning reaction", a series of complex reactions that occurs during the heating of reducing sugars or carbohydrates with amines, amino acids or proteins. Generally, melanoidins are formed by cyclizations, dehydrations, retroaldolisations, rearrangements, isomerisations, and condensations that occur over the course of the Maillard reaction.

Although melanoidins are comprised of hundred or more different compounds, which can vary from formulation to formulation, the diverse formulations have chemical and physical properties that are very similar to each other, as detailed in Examples 15-19 hereinbelow.

Melanoidins can be prepared by a number of different methods known in the art. One method of preparation of melanoidins comprises the steps of:
(a) providing a mixture of amino acids in solid form;
(b) providing a reducing sugar in solid form;
(c) combining said mixture and sugar at a 1:1 molar ratio;
d) grinding said mixture and sugar, to form a homogeneous powder; and
e) heating the powder obtained in step (d) at temperature ranging from 50 to 300° C. for time varying from weeks to seconds, depending on the reaction temperature, when lower temperatures require longer time periods, and vice versa.

Other methods for preparing melanoidins include dissolving the raw materials of steps (a) and (b) above in a suitable solvent, for example water, alcohols, acetone, or other polar solvents, followed by heating.

Melanoidins can also be isolated from melanoidin-containing substances by extraction in suitable solvents, such as water (with or without pH adjustment), alcohols, acetone, and other polar solvents, including solvent mixtures.

In one aspect, the invention provides a melanoidin obtainable by the first method described above, such as the melanoidins denoted as "M1"-"M9", or any combination thereof.

According to a specific embodiment, the melanoidins are provided to plants in a water solution. The solution may include any additional acceptable substance, including but not limited to fertilizers, and anti-pest, anti-fungal, and anti-microbial agents.

According to the invention, various melanoidin types in solution may be applied by drench and/or by spray and/or formulated with fertilizers or any other way to control a fungal disease in plants and/or to protect a plant from draught conditions and/or to improve and accelerate plant growth.

Of note, melanoidins can be used in very low amounts to induce their beneficial effect on the treated plants.

It was found according to the invention that spraying solutions M1-M3 and M6-M8 on plants was effective in controlling gray mold disease. Application by drench with the solutions M1 and M3 was superior in suppression of the disease as compared with other solutions.

Also, it was found according to the invention that various solutions of melanoidin types applied by drench and/or by spray or any other way can be used to protect plants against powdery mildew disease.

Of advantage, melanoidins were found to be effective for controlling the fungal disease also after the disease is well established.

The melanoidins can be applied to plants at a concentration range of $10^{-5}$ up to 5% w/v of the final composition or solution. In one embodiment of the invention, 0.01 and up to 0.1% w/v of the solutions of melanoidins were found to mitigate the severity of a fungal disease. These concentrations were also found effective for inducing plant drought tolerance.

In another embodiment, the melanoidins can be added to a fertilizer solution at a concentration of 0.001% w/v.

Melanoidins can be applied to the plant to be treated at any frequency, for example, between once to three times per day. Alternatively, the plant may be treated only one time. They can also be provided to the plant on a regular basis, for example, as part of the irrigation or fertilization routine. According to a specific embodiment, the melanoidins are applied twice at two different days. According to another embodiment, the treatment is supplemented by additional applications on various days.

According to the invention, the melanoidins can be applied to the plant at any stage of its life cycle, including seed, germination, vegetative growth, flowering, and fruiting.

Fractions of melanoidins were tested in the method according to the invention and both un-fractionated melanoidins and the HMW fraction are effective in controlling fungal diseases.

In one aspect, the invention provides a method for assisting with controlling the initiation and progression of plant diseases caused by fungal pathogens. The method comprises applying to the plant or a portion thereof an effective amount of a composition comprising melanoidins.

The plants that can be treated according to the invention are members of the angiosperm group, which is the group of flowering plants. According to a specific embodiment of the invention, the plants include but are not limited to members of genera that are in the Cucurbitaceae and Solanaceae families. Examples of type of plants which can be treated according to invention include but are not limited to plants belonging to the *Solanum* genus and *Cucumis* genus.

Melanoidins are effective in helping to protect plants against diseases caused by a wide variety of plant fungal pathogens. Accordingly, the invention is suitable for the elimination of various plant fungal pathogens, including powdery mildew pathogens and *Botrytis* spp. Examples of fungal pathogens which can be combated include but are not limited to: *Oidium neolycopersici, Botrytis cinerea*, and *Podosphaera xanthii*.

In one embodiment of the invention, the solutions of melanoidin significantly suppressed powdery mildew and gray mold on tomato and cucumber plants as applied by drench, by spray or in the fertilizer water.

It should be noted that melanoidins and compositions comprising thereof can be added to existing disease control materials or fertilizers.

The use of melanoidins according to the invention in organic and conventional agriculture represents a major step in assisting with controlling the initiation and progression of plant diseases caused by fungal pathogens.

More specifically, it was shown that melanoidins may reduce disease severity by up to 90%.

The melanoidin compositions according to the invention improve plants tolerance and reaction to drought stress, thereby exhibiting better plant growth, as evident by increased plant height, weight, leaf size and stem width, as well as reduced wilt. Plants treated with melanoidin prior to cessation of irrigation demonstrate continues growth in spite of lack of irrigation.

Additionally, the compositions are useful for improving plant recovery from drought stress. Application of melanoidin solution to plants under drought stress reduces the wilt severity and the number of mortal leaves.

In a further aspect of the invention, melanoidins were found to have a continuous and positive effect on plant growth, as evident by a significant increased plant height, number of joints, leaf size and number of flowers. Additional plant characteristics that are improved by the method and compositions of the invention include seed germination, and root initiation and elongation.

Suitable forms for using melanoidins are manifold, including but not limited to: (i) dry powder or granules to be mixed up in any plant-suitable solvent with or without added surfactant and applied as a liquid either by soil drench or foliar spray; (ii) application directly to soil surface as powder or granules; (iii) incorporation into slow release solids for soil application; (iv) compounding together with other plant disease suppressive active ingredients; (v) compounding together with fertilizers; (vi) adding to soil amendments, and much more.

In order to apply the melanoidins to a plant, they may be formulated into a composition which may include a suitable inert diluent or carrier.

The melanoidins according to the invention may be applied by any of the known means of applying agents to a plant. For example, it may be applied, formulated or unformulated, to any portion or part of the plant, including the foliage, stems, branches or roots, to the seed before it is planted or to other media in which plants are growing or are to be planted (such as the soil), directly or it may be sprayed on, dusted on, applied by dipping, applied through distribution or incorporation of a composition (such as a granular composition) in soil or an aqueous environment.

The melanoidins according to the invention may also be sprayed onto vegetation or applied by land or aerial irrigation systems.

The melanoidins may be used in mixtures with fertilizers (for example nitrogen-, potassium- or phosphorus-containing fertilizers), which can be in the form of solution or solid. The mixtures contain between 0.0001 and 0.01% by weight of the melanoidins, more specifically, 0.001% of the final fertilizer.

Advantages of melanoidins include the following:
Ease and reproducibility of synthesis.
Ability to easily synthesize large amounts without specialized equipment.
Melanoidins, being a common component of a large variety of prepared foods (for example honey, coffee, cake, fried onions, browned meat and much more) are non-toxic materials (GRAS, generally regarded as safe).
Melanoidins would not present any risks to farm workers at any stage of use (preparation, application, harvesting) or to consumers of the agricultural produce. In the soil, melanoidins break down to non-toxic, naturally occurring compounds, and hence would not present any environmental risks or dangers of buildup in the soil.
Melanoidins are highly versatile in that they can be applied in many ways, for example, including but not limited to, foliar spray, soil drench, dry powder application to soil, granule application to soil.

The invention will now be described with reference to specific examples and materials.

EXAMPLES

Materials and Methods
Preparation of Melanoidins

A solid commercial protein hydrolysate (mixture of amino acids prepared by splitting a protein with acid, alkali, or enzyme) was ground together with one or more solid reducing sugars at a 1:1 weight ratio of hydrolysate to sugar, obtaining a fine homogeneous powder. Grinding at room temperature was carried out quickly to minimize water absorption by the hydrolysates, which are hygroscopic (absorb water from the air). The mixture was heated in a porcelain dish for 8 minutes and 30 sec at 150±1° C. in a pre-heated oven, and then transferred to a desiccator with silica gel for cooling to room temperature. During the heating, the amino acids in the hydrolysate reacted with the sugars to form brown-colored melanoidins via the Maillard reaction. The cooled melanoidins were gently ground and transferred to hermetically sealed vials for storage.

In general, any combination of individual amino acid or mixture of amino acids as in a hydrolysate (e.g., made from beef, casein, soy, rice etc.) and reducing sugar (e.g., monosaccharides such as glucose, galactose, or xylose, etc.) disaccharides (e.g., lactose or maltose, etc.), or polysaccharides can react to form melanoidins via the Maillard reaction. Synthesis conditions including temperature, heating time and solvent (dry, water, alcohol or other solvent) can be varied. The 1:1 weight ratio was chosen because it represented an approximately 1:1 molar ratio of amino acid to reducing sugar (considering the weight % mixture of amino acids in a protein hydrolysate and their individual molecular weights, as compared with the molecular weight of the chosen reducing sugar(s)). This approximation, while not exact, works well for the different hydrolysates and reducing sugars tested (Table 1).

In general, the elementary composition of melanoidins differs markedly depending on the sugars and amino acids that are used. Reaction conditions also have a significant influence on the composition of the melanoidins. However, the fundamental composition of model melanoidins under constant reaction conditions is only negligibly influenced by the molar ratio of the reactants [Cämmerer B. and Kroh L. W., Food chemistry, 1995. 53(1):55-59].

In the following examples, several commercial hydrolysates (see Table 1) were tested in mixtures with two reducing sugars (glucose and xylose, both separately and together). Listed below are the different hydrolysate and sugar combinations which were tested:

TABLE 1

Melanoidins solutions

| Name of the tested melanoidins solution | Hydrolysate type | Sugar type |
|---|---|---|
| M1 | Proteose Peptone # 3 CONDA Pronadisa Cat. # 1607.00 | D-(+)-Glucose; Sigma-Aldrich Cat. # G8270; purity >99.5% |
| M2 | Bacto ™ BD, Peptone Cat. # 211677 | D-(+)-Glucose; Sigma-Aldrich Cat. # G8270; purity >99.5% |
| M3 | Bacto ™ BD, Tryptone pancreatic digest of casein Cat. # 211705 | D-(+)-Glucose; Sigma-Aldrich Cat. # G8270; purity >99.5% |
| M4 | Proteose Peptone # 3 CONDA Pronadisa Cat. # 1607.00 | D-(+)-Xylose; Sigma-Aldrich Cat. # X1500; purity >99% |
| M5 | Bacto ™ BD, Peptone Cat. # 211677 | D-(+)-Xylose; Sigma-Aldrich Cat. # X1500; purity >99% |
| M6 | Bacto ™ BD, Tryptone pancreatic digest of casein Cat. # 211705 | D-(+)-Xylose; Sigma-Aldrich Cat. # X1500; purity >99% |
| M7 | Proteose Peptone # 3 CONDA Pronadisa Cat. # 1607.00 | Glucose:xylose 1:1 (same sugars as in previous) |
| M8 | Bacto ™ BD, Peptone Cat. # 211677 | Glucose:xylose 1:1 (same sugars as in previous) |
| M9 | Bacto ™ BD, Tryptone pancreatic digest of casein Cat. # 211705 | Glucose:xylose 1:1 (same sugars as in previous) |

For the following experiments, the melanoidins were tested at concentrations of 0.01, 0.03, and 0.1% in water. Different batches of a given preparation were synthesized to confirm repeatability of the synthesis process and biological effect. Each consecutive batch is numbered consecutively (e.g., M1, M1.1, M1.2 are the $1^{st}$, $2^{nd}$, and $3^{rd}$ batches of M1).

In one example, high molecular weight (HMW) melanoidins were concentrated using a 3000 Dalton ultrafiltration membrane. The HMW retentate was then diluted with double distilled water and re-concentrated by ultrafiltration using the same membrane, twice. The final retentate (>3000 Dalton) containing only HMW melanoidins was dried by lyophilizing after shock freezing in liquid $N_2$. The ultrafiltration procedure followed by rinsing, known as diafiltration, effectively removes remnants of low molecular weight reactants, if there are any. The cleaned high molecular weight fraction is referred to as "cleaned" materials or high molecular weight (HMW) melanoidins below.

Disease Control Experiments

Plants

Plants of tomato and cucumber were grown from seeds in a nursery and transplanted into 1 liter pots at 40 to 50 days after seeding in an unheated greenhouse. Plants were fertilized proportionally with drippers 2-3 times per day with 5:3:8 NPK fertilizer (irrigation water was planned to have total N, P and K concentrations of 120, 30 and 150 mg/L, respectively; EC 2.2 dS/m), allowing for 25-50% drainage. Plants were maintained at 20 to 30° C. with natural light, and relative humidity of 50-90% in a pest- and disease-free greenhouse during the growth period and then transferred to an area where diseases were allowed to develop following pathogen infection on intact or detached leaves as described below.

Pathogens: Growth, Harvesting, Infection and Evaluation of Conferred Disease Severity Gray Mold Inducing Pathogen Botrytis cinerea [Pers.:Fr. [Teleomorph: Botryotinia fuckeliana (de Bary) Whetzel] (isolate BcI16; [Swartzberg D. et al., Eur. J. Plant Pathol., 2008, 120:289-297])] was cultured on potato dextrose agar (PDA, Difco, Detroit, Mich.) in 90 mm diam. petri dishes containing 15 ml PDA each and incubated at 20° C. The inoculum was maintained on PDA and transferred every two weeks. Gray mold conidia were harvested from 10 to 14 day-old cultures by agitating 1 $cm^2$ of agar bearing mycelium and conidia in a glass tube with tap water. The suspension was then filtered through cheesecloth. The concentration of conidia was determined using a haemocytometer and a light microscope, and adjusted to $5 \times 10^5$ conidia/ml. Since B. cinerea conidia need carbon and phosphate for germination and penetration, 0.1% glucose was added to the final conidial suspension together with 0.1% $KH_2PO_4$. These supplements have been shown to facilitate germination of B. cinerea conidia and subsequent leaf infection.

Plant attached tomato leaves were examined. Whole plants were kept in a humidity chamber at 20±1° C., 97±3% RH, and 1020 lux light intensity. Plants were infected by spraying the whole plant with 2 ml of a $5 \times 10^5$ conidia/ml suspension.

Disease severity was evaluated on each plant using a pictorial key; 0=no infection (all leaves are symptomless) and 100=all leaves are fully covered by gray mold symptoms.

At all times, the temperature of the growth room was kept at 20±1° C. and 75-90% RH.

Powdery Mildew Inducing Pathogen

The tomato powdery mildew pathogen Oidium neolycopersici Kiss was isolated from young leaves of tomato plants grown in a commercial greenhouse. Conidia of this pathogen were harvested by rinsing infected leaves with sterile water. For the artificial infection of tomato leaves (growth chamber experiments), the concentrations of these conidial suspensions were determined under a light microscope with a haemocytometer. The concentrations of all suspensions were adjusted to $10^4$ conidia/ml and then sprayed onto plants using a volume of 5 ml per plant. All suspensions were applied to the plants within 10 to 15 min from the time of harvesting of the conidia. Suspensions were applied with a hand-held spray bottle and plants were left to dry for up to 30 min. At all times, the temperature of the growth room was kept at 20±1° C. and 75-90% RH, and 2030 lux light intensity.

Tomato powdery mildew severity was evaluated using a pictorial key; 0=no infection (leaves appear healthy) and 100=leaves covered by powdery mildew symptoms. Severity was evaluated at three different plant heights and averaged for the entire plant. Most of the disease symptoms were observed on the leaves and not on other plant parts, thus leaf infection was monitored.

Cucumber Powdery Mildew

The cucumber powdery mildew pathogen Podosphaera xanthii [(Castagne) Braun & Shishkoff [=Sphaerotheca fusca (Fr.) Blumer=S. fuliginea (Schlechtend.:Fr.) Pollacci]] was harvested from naturally infected plants in crops or from young leaves of cucumber plants grown in a greenhouse. Conidia of this pathogen were harvested by rinsing infected leaves with sterile water.

For the experimental infection of cucumber leaves (growth chamber experiments), the concentrations of these conidial suspensions were determined under a light microscope with a haemocytometer. The concentrations of all suspensions were adjusted to $10^4$ conidia/ml and then sprayed onto plants using a volume of 5 ml per plant. All suspensions were applied to the plants within 10 to 15 min from the harvesting time of the conidia. Suspensions were applied with a hand-held spray bottle and plants were left to dry for up to 30 min. At all times, the temperature of the growth room was kept at 20±1° C. and 75-90% RH, and 2030 lux light intensity.

Cucumber powdery mildew severity was evaluated using a pictorial key; 0=no infection (all leaves appear healthy) and 100=all leaves covered by powdery mildew symptoms. Severity was evaluated at three to six different plant heights and averaged for the entire plant. Most of the disease symptoms were observed on the leaves and not on other plant parts, thus leaf infection was monitored.

Melanoidins Treatment

Melanoidins treatment consisted of either spray or drench at 3 mL/plant. Control plants were not infected, treated by water and kept under the same conditions as mentioned above.

Statistical Analysis

Treatments in experiments were replicated 5-10 times. Replicates of each treatment were arranged randomly. Disease severity data in percentages were arcsin-transformed before further analysis. Disease severity data were analyzed using ANOVA and Fisher's protected LSD test. Standard errors (SE) of the means were calculated and disease levels were statistically separated (P≤0.05) following a one-way analysis of variance. A control experiment presents the severity of the disease with application of only water without the melanoidin.

Drought Tolerance Experiments

Plants

Plants of tomato were grown from seeds and transplanted into 1 liter pots containing perlite at 40 to 50 days after seeding. Plants were fertigated proportionally with drippers 2-3 times per day with 5:3:8 NPK fertilizer (irrigation water was planned to have total N, P and K concentrations of 120, 30 and 150 mg/L, respectively; EC 2.2 dS/m), allowing for 25-50% drainage. Plants were maintained at 20 to 30° C. in a pest- and disease-free greenhouse during a growth period of two months and then transferred to an area where irrigation was not used, temperature was 22±1° C., illumination duration was 12 h/day and the entire pot volume was enclosed in a plastic bag to avoid evaporation from the root zone.

Treatments and Evaluations

During a period of 21 days with no irrigation, measurements of leaf length (in cm), terminal leaflet area (cm$^2$), plant weight (in gram), and wilt severity (on a scale of 0-100% where 0=no wilt and 100=plant totally wilted) were taken.

Following the 3 weeks of no irrigation, plants were irrigated to field capacity, allowed to recover and gain turgor for 4 hours and then wilt severity was measured again and the number of live leaves was counted.

The solution of melanoidins was sprayed on plants or applied as drench to the root zone in concentrations of 0.01 and 0.1% at 3 days before and on the day of irrigation cessation (−3 and 0). Additionally, in some of the experiments the spray treatments included two more sprays, on days 7 and 14 after irrigation cessation (+7, +14). Volume of applied solution in drench was 5 ml and 2 ml in spray per plant. Control plants were treated with water drench or spray in the same way as the treatments with melanoidins. M1 was used in this experiment. Melanoidins were dissolved in water to the desired concentration.

Growth Experiments

Plants

Tomato seedlings approximately 30-40 days old were obtained from a nursery and transplanted into specially-designed 10 liter pots whereby the lower third was lined with glass fiber wool, leading to a drain pipe also filled with glass fiber wool. The purpose of the glass fiber wool was to improve drainage from the growing medium, which was clean quartz sand. Plants were fertigated (fertilized via the irrigation water) proportionally with drippers 2 times per day in accordance with the plant needs. The electrical conductivity (EC) of the leachate was monitored routinely, and irrigation amount was adjusted so that the leachate EC was equal to that of the input EC, thus enabling sufficient water application and avoiding accumulation of salts in the sand.

Treatments and Evaluations

The fertilizer solution consisted of 0.2% fertilizer, 4-2.5-6 (N—$P_2O_5$—$K_2O$; to give 80:50:120 mg/L in solution). The fertilizer also contained 2% Ca, 0.5% Mg, and additional microelements. Half the plants were fertilized with fertilizer solution that had 0.001% (10 mg/L) M1 added, and the other half received only fertilizer. There were 7 replicate plants per treatment. Plants were grown in net house over a period of 48 days after transplanting.

Total N content of M1 is 7%, which means it added an additional 0.7 mg/L N to the fertilizer solution. This is a negligible amount compared with the fertilizer N (80 mg/L).

Example 1

Effect of Various Solutions of Melanoidins on Gray Mold Severity in *Botrytis cinerea* Infected Tomato Plants Plants were infected by *Botrytis cinerea* suspension (as described in the "Materials and Methods" section) 25 days after planting. Solutions of various melanoidin types (see table 1 for key) at 0.1% (0.1 g melanoidins per 100 ml) were either sprayed or drenched twice, 3 days and 1 hour before infection. Severity of the disease was evaluated 11 days following infection and incubation at high humidity conditions.

Figure 1A:
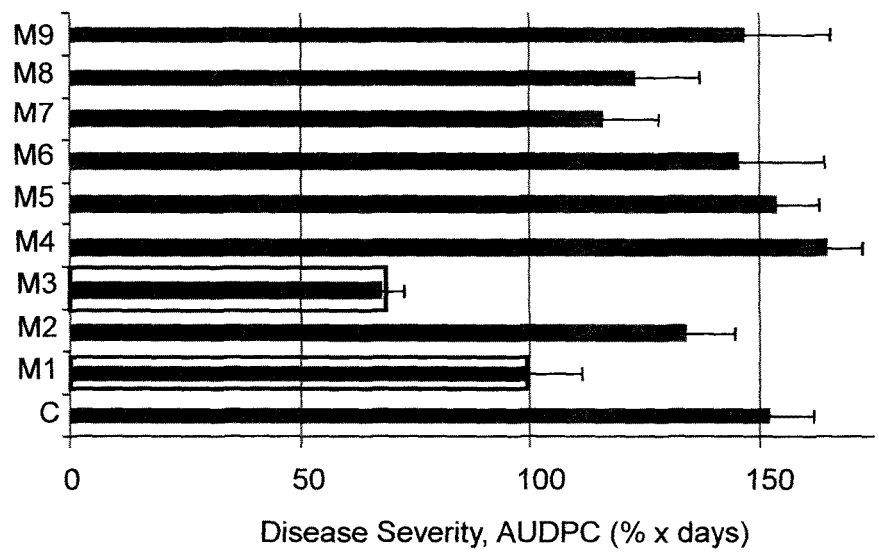
FIG. 1A-1B show the effect of 0.1% of different melanoidins (M1-M9) applied by drench (FIG. 1A) or spray (FIG. 1B) on the severity of gray mold (*Botrytis cinerea*) in tomato, 11 days after infection. Disease severity is presented as area under disease progress curve (AUDPC) over the course of 11 days. Bars represent standard error.
Figure 1B:
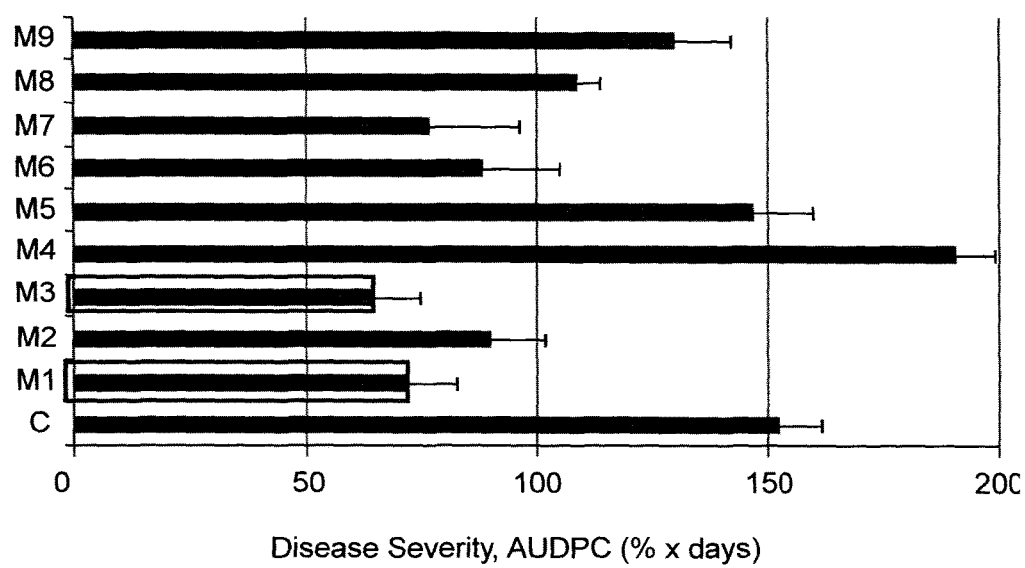

It was found that sprayed solutions M1-M3 and M6-M8 on the tomato plants were effective in decreasing the disease severity. Application by drench with the solutions M1 and M3 was superior in disease suppression as compared with other solutions (FIG. 1).

Example 2

Effect of Spray of Solutions of Various Melanoidin Types on Powdery Mildew Severity in *Oidium neolycopersici* Infected Tomato Plants Tomato plants were infected by *Oidium neolycopersici* (as indicated in the "Materials and Methods" section) 33 days after planting. The plants were treated twice by spray of 0.1% melanoidins (See Table 1 for key) solutions 3 days and 1 hour before infection. Evaluation of tomato powdery mildew severity was carried out through 19 days after infection.

It was found that spraying with 0.1% of various melanoidins suppressed tomato powdery mildew (FIG. 2).

Example 3

Effect of Solutions of Various Melanoidin Types Applied by Spray and by Drench on Powdery Mildew Severity in *Oidium neolycopersici* Infected Tomato Plants Tomato plants were infected by *Oidium neolycopersici* 35 days after planting. The plants were treated by drench or by spray of 0.1% melanoidin solutions (see Table 1 for key) 3 days and 1 hour before infection. Evaluation of tomato powdery mildew severity was carried out through 23 days after infection.

It was found that spraying with 0.1% solutions of various melanoidin types suppressed tomato powdery mildew, yet M1.1 and M2 were significantly more effective.

It was also found that application by drench with 0.1% solutions of M1.1 and M3.1 suppressed tomato powdery mildew (FIG. 3).

Example 4

Effect of Spray of Solutions of Various Melanoidin Types on Powdery Mildew Severity in *Oidium neolycopersici* Infected Tomato Plants Tomato plants were infected by *Oidium neolycopersici* 30 days after planting. The plants were treated by spraying 0.1% melanoidins solutions 3 days and 1 hour before infection. Evaluation of tomato powdery mildew severity was carried out through 18 days after infection.

It was found that spraying with 0.1% solutions of various melanoidin types suppressed tomato powdery mildew (FIG. 4).

Example 5

Effect of Melanoidins Concentration on Powdery Mildew Severity in *Oidium neolycopersici* Infected Tomato Plants Solutions of two kinds of melanoidins were applied by spraying at two concentrations. Plants were infected by conidia suspension of *Oidium neolycopersici* 20 days after planting. Melanoidin solutions at concentration range of 0.03-0.1% were applied twice, 3 days and 1 hour before infection. Disease was evaluated 42 days after infection.

It was found that both concentrations of the two melanoidin types (see Table 1 for key) applied as spray were effective in suppressing tomato powdery mildew (FIG. 5).

Example 6

Effect of HMW Melanoidins on Gray Mold Severity in *Botrytis cinerea* Infected Tomato Plants The action of the cleaned and fractionated melanoidins (prepared as described above) was compared with that of the regular melanoidins in order to test if low molecular weight residual reactants or other low molecular weight Maillard reaction products could be responsible for the disease suppression, rather than the polymeric melanoidins. Both types ("cleaned" and "not-cleaned") were applied by spraying or drench. Plants were infected by using a conidia suspension of *Botrytis cinerea* 40 days after planting. Melanoidin solutions at concentration of 0.03% were applied twice, 3 days and 1 hour before infection. Disease was evaluated 7 days after infection and incubation under conditions of high relative humidity.

It was found that both melanoidin preparations, the "cleaned" and the "not cleaned" were equally effective in suppressing tomato gray mold. HMW melanoidin solution was effective in controlling the disease when applied by spray or drench (FIG. 6). This experiment shows that melanoidins are indeed the active component, as opposed to any (possible) residual reactants or low molecular weight Maillard products.

Example 7

Effect of Drench and Spray of Solutions of Various Melanoidin Types on *Podosphaera xanthii* Powdery Mildew Development in Cucumber Plants Cucumber plants were treated by melanodins at 3, 11 and 18 days after planting. *Podosphaera xanthii* powdery mildew that naturally developed on the plants was evaluated during 23 days after planting.

It was found that powdery mildew was suppressed by drench of 0.1% solutions of various melanoidin types (see Table 1 for key) and by spray of 0.03-0.1% solutions of various melanoidin types (FIG. 7).

Example 8

Effect of HMW and Non-fractioned Solution of a Melanoidin Type on *Podosphaera xanthii* Powdery Mildew Severity in Infected Cucumber Plants Cucumber plants were infected by *Podosphaera xanthii* 33 days after planting. HMW and non-fractioned melanoidin solutions were applied as drench at the concentration of 0.03%. Severity of the disease was evaluated during 36 days after infection.

It was found that both HMW and non-cleaned solution of a melanoidin type (see Table 1 for key) significantly suppressed cucumber powdery mildew severity when applied as drench of 0.03% solutions (FIG. 8).

Example 9

Effect of Melanoidins on Plant Weight Under Drought Conditions

Tomato plants were treated by a solution of 0.01-0.1% M1 or water (control), either by spraying on the canopy or drenching to the root zone. Three weeks after irrigation cessation, the weight of the plants was increased in the drench treatment (FIG. 9) and by the spray treatments that were applied at days −3, 0, 7 and 14 relative to cessation of irrigation (FIG. 10).

The results demonstrate continues growth of plants in the melanoidin treatment in spite of the lack of irrigation.

Example 10

Effect of Melanoidins on Leaf Growth Under Drought Conditions

Tomato plants were treated by a solution of 0.01-0.1% M1 or water (control), either by spraying on the canopy or drenching to the root zone. Two weeks after the cessation of irrigation, the leaf length was increased by the drench and spray treatments that were applied at days −3, 0 relative to cessation of irrigation (FIG. 11).

The results demonstrate the continued growth of the plants treated by the melanoidin solutions in spite of the lack of irrigation.

Example 11

Effect of Melanoidins on Plant Wilt after Re-watering Following Drought

Tomato plants were treated by a solution of 0.01-0.1% M1 or water (control), either by spraying on the canopy or drenching to the root zone. The plants were left for 21 days with no watering, and were then re-watered. Four hours after re-watering, the severity of wilt (FIG. 12) and the number of live leaves (FIG. 13) were evaluated. The spray and drench treatments with melanoidin solutions reduced the wilting severity of the tomato plants (FIG. 12) and the mortality of leaves (FIG. 13).

The results demonstrate the positive effect of melanoidins on plants recovery from the drought effect.

Example 12

Effect of Melanoidins on Tomato Plant Height, Number of Joints and Leaf Length

Tomato plants were fertilized with fertilizer solution that had 0.001% (10 mg/L) M1, or fertilizer solution alone as control. The addition of M1 to the fertilizer solution on a regular basis had a continued and positive effect on plant growth, as expressed in terms of plant height (FIG. 14A), number of joints (FIG. 14B), and leaf length (FIG. 14C). The increase in number of joints and leaf size that accompanied the increase in plant height indicates that, while the plants were taller under melanoidin treatment, they were not etiolated.

Example 13

Effect of Melanoidins on Number of Flowers in Tomato Plants

Tomato plants were fertilized with fertilizer solution that had 0.001% (10 mg/L) M1, or fertilizer solution alone as control. The number of flowers per plant beginning from 33 days after transplanting is shown in FIG. 15. The results demonstrate a significantly larger number of flowers in the melanoidin treated plants.

Example 14

Effect of Melanoidins Applied in Fertigation Solution on Gray Mold Severity in *Botrytis cinerea* Infected Tomato Plants Tomato plants were fertilized with fertilizer solution that had 0.001% (10 mg/L) M1, or fertilizer solution alone as control. Leaves were detached from the plants 4 weeks following transplanting and 8 weeks following transplanting. The detached leaves were infected by *Botrytis cinerea* suspension (as described in the "Materials and Methods" section).

It was found that M1 given in the fertilizer water protected the tomato plants from gray mold infection both at 4 weeks and 8 weeks following transplanting, thus showing it is effective through the lifetime of the plant (FIG. 16).

Example 15

Characterization of Melanoidins by UV-Vis

UV-Vis absorbance spectra of 100 mg/L of melanoidin solutions in double distilled water were measured on a UV-Vis spectrophotometer ThermoScientific (Genesys 10 UV) between 190 to 700 nm.

The results presented in FIG. 17 show that the spectra for all melanoidin solutions are very similar, demonstrating maximal absorbance at about 200 nm followed by a sharp decline in absorbance to about 240 nm, an increase in absorbance to about 280-290 nm, and a gradual decline to 700 nm.

Example 16

Characterization of Melanoidins by Fluorescence Excitation-emission Spectra

Spectra of different melanoidins (M1, M3, M7 and M9) were collected on a Shimadzu RF-5301PC spectrofluorometer over the excitation range of 210-590 nm and emission range of 220 to 600 nm. Excitation and emission slit of 5 nM, at a high sensitivity, resolution of 2 nm, and increment of 5 nm. Aqueous solutions were 22 mg/L.

The results presented in FIG. 18A (M1), FIG. 18B (M3), FIG. 18C (M7) and FIG. 18D (M9) demonstrate that all the spectra are very similar, with a dominant peak at excitation/emission wavelengths of 350/425 nm, a secondary peak at excitation/emission wavelengths of 225/450 nm, and a small tertiary increase at excitation/emission wavelengths of 275/360 nm.

Example 17

Characterization of Melanoidins: Aqueous Solubility at 25° C.

Different melanoidins (M1 and M3) were found have solubility of >70 g/100 mL water at 25° C.

The high water solubility demonstrates the essentially hydrophilic nature of melanoidins, and reflects their origin as a product of reaction between hydrophilic sugars and amino acids.

Example 18

Characterization of Melanoidins: Aqueous Surface Tension of M1 as a Function of Concentration Surface tension was measured at 20° C. by means of a Delta-Pi microtensiometer (Kibron, Helsinki, Finland) based on the Wilhelmy method and utilizing a small diameter (0.51 mm) special alloy wire.

According to the results shown in FIG. 19, melanoidins have very little surface activity, as shown by the fact that at concentrations as high as 1000 mg/L, the surface tension of the solution is not reduced significantly below that of pure water (72.8 mN/m at 20° C.). Even at its most concentrated, approximately 100 g/100 mL, the melanoidin solution surface tension is only reduced to about 45 mN/m. This behavior can be contrasted with surfactants, which can substantially and significantly reduce the surface tension of water when present at very low concentrations. Surfactants are amphiphilic organic compounds, meaning they have both hydrophobic groups and hydrophilic groups in the molecule, allowing them to accumulate on the surface of water and reduce the surface tension. Melanoidins, as consistent with their high water solubility, are not amphiphilic and do not easily accumulate at water-air surfaces.

Example 19

Characterization of Melanoidins: FTIR

FTIR absorbance spectra of KBr pellets prepared with 0.3% w/w of melanoidins in KBr were recorded between 400 and 4000 $cm^{-1}$ with one hundred scans averaged with a resolution of 4 $cm^{-1}$ (Bruker Tensor 27 FTIR Spectrometer).

The results shown in FIG. 20 indicate that all the different melanoidins preparations (M1, M3, M7, and M9) are similar. The FTIR spectra retain the general characteristics of that of the precursor sugar(s), with certain changes due to the reaction with amino acids.

The invention claimed is:

1. An aqueous solution for applying to a plant to improve resistance to a plant fungal pathogen in the plant or drought tolerance in the plant or both, the solution comprising melanoidins at a concentration of 0.001-0.1% w/v, wherein said melanoidins are a product of the Maillard reaction in a solid mixture of a reducing sugar with a protein hydrolysate at about a 1:1 weight ratio heated to between 50 and 300° C.

2. The solution according to claim 1, wherein said solution is adapted for application to the plant by spray, drench, irrigation, or fertigation.

3. The solution according to claim 1, wherein said plant belongs to the Solanceae family or the Cucurbitaceae family.

4. The solution according to claim 1, wherein said fungal pathogen is a powdery mildew pathogen or a gray mold pathogen.

5. The solution according to claim 1, wherein said fungal pathogen is selected from *Oidium neolycopersici*, *Podosphaera xanthii* and *Botrytis cinerea*.

6. The solution of claim 1, comprising melanoidins at a concentration of 0.001% w/v in water.

7. The solution of claim 1, comprising melanoidins at a concentration of 0.01% w/v in water.

8. The solution of claim 1, comprising melanoidins at a concentration of 0.1% w/v in water.

9. The solution of claim 1, wherein said reducing sugar is D+glucose.

10. The solution of claim 1, wherein said reducing sugar is D+xylose.

11. The solution of claim 1, wherein said protein hydrolysate is a product of enzymatic digestion of animal tissues.

12. The solution of claim 1, wherein said protein hydrolysate is a product of enzymatic digestion of casein.

13. The solution of claim 1, wherein said melanoidins are >3000 Dalton.

14. The solution of claim 1, wherein said solid mixture is heated to 150±1° C.

15. The solution of claim 1, comprising melanoidins at a concentration of 0.01% w/v in water, wherein said reducing sugar is D+glucose and said protein hydrolysate is a product of enzymatic digestion of animal tissues and said solid mixture is heated to 150±1° C.

16. A method for improving at least one property in a plant, the property selected from the group consisting of resistance to a plant fungal pathogen and drought tolerance, the method comprising applying the aqueous solution of claim 1 to the plant in an amount effective to improve the property in the plant.

17. The method according to claim 16, wherein said solution is applied by spray, drench, irrigation, or fertigation.

18. The method according to claim 16, wherein said solution is applied with the irrigation or fertigation water.

19. The method according to claim 16, wherein said plant belongs to the Solanceae family or the Cucurbitaceae family.

20. The method according to claim 16, wherein said fungal pathogen is a powdery mildew pathogen or a gray mold pathogen.

21. The method according to claim 16, wherein said fungal pathogen is selected from *Oidium neolycopersici*, *Podosphaera xanthii* and *Botrytis cinerea*.

22. The method according to claim 16, wherein said solution is applied more than once.

23. The method according to claim 16, wherein said solution is applied at least twice on different days.

24. The method according to claim 16, wherein said solution is applied to any plant organ at any stage of its life cycle.

25. A method for improving a property in a Solanceae family or the Cucurbitaceae family plant, the property selected from the group consisting of resistance to a plant fungal pathogen and drought tolerance, the plant fungal pathogen selected from the group consisting of *Oidium neolycopersici, Podosphaera xanthii* and *Botrytis cinereal*, the method comprising applying the aqueous solution of claim 15 to the plant in an amount effective to improve the property in the plant.

* * * * *